US006686174B1

United States Patent
Fang et al.

(10) Patent No.: US 6,686,174 B1
(45) Date of Patent: *Feb. 3, 2004

(54) METHOD AND CONSTRUCTS FOR INHIBITING PROTEIN EXPRESSION IN BACTERIA

(75) Inventors: Li Fang, Burlingame, CA (US); Weinning Jiang, Forest Hills, NY (US); Masanori Mitta, Kyoto (JP); Masayori Inouye, Piscataway, NJ (US)

(73) Assignee: The University of Medicine and Dentistry of New Jersey, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/293,427

(22) Filed: Apr. 16, 1999

Related U.S. Application Data

(63) Continuation of application No. PCT/US97/24151, filed on Dec. 19, 1997, which is a continuation of application No. 08/769,945, filed on Dec. 19, 1996, now Pat. No. 5,981,280.
(60) Provisional application No. 60/013,922, filed on Mar. 22, 1996.

(51) Int. Cl.[7] .................. C07H 21/02; C07H 21/04; C12N 1/21; C12N 15/09; C12N 15/70
(52) U.S. Cl. .............. 435/69.1; 435/252.3; 435/252.33; 435/320.1; 435/471; 536/23.1; 536/24.1; 536/24.5
(58) Field of Search .................. 435/6, 29, 252.3, 435/252.33, 320.1, 471, 476; 536/23.1, 23.7, 24.1, 24.3, 24.32, 24.5

(56) References Cited

U.S. PATENT DOCUMENTS 5,654,169 A * 8/1997 Oppenheim et al. ....... 435/69.1
5,714,575 A * 2/1998 Inouye et al. ............... 530/300
5,981,280 A * 11/1999 Fang et al. .................. 435/471

OTHER PUBLICATIONS

Sprengart et al. The downstream box: an efficient and independent translation initiation signal in *Escherichia coli*. EMBO J. 15(3): 665–674 (1996).*

* cited by examiner

*Primary Examiner*—Andrew Wang
*Assistant Examiner*—Thomas G Larson
(74) *Attorney, Agent, or Firm*—Schnader Harrison Segal & Lewis LLP

(57) ABSTRACT

A method of inhibiting the translation of bacterial mRNA is disclosed. The method comprises overexpressing in a bacterium an mRNA which contains a sequence which is complementary to the anti-downstream box region of the 16S rRNA. RNA and DNA constructs for the overexpression of the mRNA of the invention are disclosed. Further, there are disclosed isolated DNA constructs that direct the prolonged expression of a heterologous gene in a cold-shocked bacterium at reduced temperature. The construct can comprise a promoter region of a cold-shocked inducible gene. The replication vehicle comprising such DNA constructs and a method for overexpressing a heterologous gene in a bacterium transformed with such a replication vehicle are also disclosed.

52 Claims, 23 Drawing Sheets cspB (+4−+27)  UCGGUUUGAAGAACAGACGAUAUA
cspA (+1−+24)  ACGGUUUGACGUACAGACCAUUAA
csdA (+42 +65) AAUAGCUGACGUACACAAUCAGCC Consensus :   UGACGUACAGA

```
           *         *         *         *
AAGCTTCGATGCAATTCACGATCCCGCAGTGTGATTTGAGGAGTTTCAATGGAATATAA    60
           *         *         *         *
AGATCCAATGCATGAGCTGTTGAGCAGCCTGGAACAGATTGTTTTAAAGATGAAACGCA   120
           *         *         *         *
GAAAATTACCCTGACGGCACAGAACAACGTCCTGTACCGAAATTGAGCAGTTACGAAAAGG  180
           *         *         *         *
GACAGGATTAAAAAATGGATGATTTCGCCCGGGTTTTGGGCGTATCAGTCGCCATGGTAAA  240
           *         *         *         *
GGAATGGGAATCCAGACGCGTGAAGCCTTCAAGTGCCGAACTAAAAATTGATGCGTTTGAT  300
           *         *         *         *
TCAAGCCAACCCGGCATTAAGTAAGCAGTTGATGGAATAGACTTTATCCACTTATGCTGT  360
           *         *         *         *
TTACGGTCCTGATGACAGACCGTTTTCCAACCGATTAATCATAAATATGAAAAATAATTG  420
           *         *         *         *
TTGCATCACCCGCCAATGCGTGGCTTAATGCACATCAACGGTTTGACGTACAGACCATTA  480
```

| FIG. 17 |
|---|
| FIG. 17a |
| FIG. 17b |
| FIG. 17c |

FIG. 17a

```
                              *                             *                             *
AAGCAGTGTAGTAAGGCAAGTCCCTTCAAGAGTTATCGTTGATACCCTCGTAGTGCACA    540

*                             *                             *
TTCCTTTAACGCTTCAAAATCTGTAAAGCACGCCATATCGCCGAAAGGCACACTTAATTA    600

*                             *                             *
TTAAAGGTAATACACT  ATGTCCGGTAAAATGACTGGTATCGTAAAATGGTTCAACGCT    658
                  MetSerGlyLysMetThrGlyIleValLysTrpPheAsnAla

*                             *                             *
GACAAAGGCTTCGGCTTCATCACTCCTGACGATGGCTTAAAGATGTGTTCGTACACTTC    718
AspLysGlyPheGlyPheIleThrProAspAspGlySerLysAspValPheValHisPhe

*                             *                             *
TCTGCTATGCAGAACGATGGTTACAAATCTCTGGACGAAGGTCAGAAGTGTCCTTCACC    778
SerAlaIleGlnAsnAspGlyTyrLysSerLeuAspGluGlyGlnLysValSerPheThr

*                             *                             *
ATGGAAAGCGGGCTAAAGGCCCGGCAGCTGGTAACGTAACCAGCCTGTAA  TCTCTGC    836
IleGluSerGlyAlaLysGlyProAlaAlaGlyAsnValThrSerLeu  -

*                             *                             *
TTAAAAGCACAGAATCTAAGATCCCTGCCATTTGGCGGGGATTTTTTATTTGTTTTCAG    896
```

FIG. 17b

```
                                                                    *
GAAATAAATAATCGATCGGCGTAATAAAATCTATTATTTTGTGAAGAATAAATTTGG    956
                                                                    *
GTGCAATGAGAATGCGCAACGCCGTAAGTAAGGCGGGAATAATTCCCGCCGAAGACTCT 1016
                                                                    *
TACTGTTTCAATTTGCAGGCTAAAAACGCCGCCAGCTCATAACTCTCCTGTTTAATATGC 1076
                                                                    *
AATTCACACAGTGAATCTCTTATCATGCAGGTGAAAAATAAAAGCGTGAAACAAATCACT 1076
                                                                    *
ATTAAAGAAAGTAATGTATATTTCTGCGCATTCCAGCTCTGTGTTGATTTCACGAGTATG 1136
 *
TAGTGCACC 1205
```

FIG. 17c cspB

```
         *         *         *         *         *         *
AGCTTTAATATAGCTCATGAAAGGTAAACATTGGCAGCTGAAGGGCCACGCAGACCATTT    60
         *         *         *         *         *         *
ATCCGGCAAAATTCCACGCGTAATCCGGTGGTAATTCTTCTGCATCGCGGAGATTGAGC   120
         *         *         *         *         *         *
GCTGAAACATGAAGCTGGACATCGATACGACCATCGGATGGGGTGATAAGACCCTTGCCG   180
         *         *         *         *         *         *
CTTTTGCCGTCAAAGGTTTTGACAATTCCTGTCATTTTACGGGACAAAAAATTCCTTAA   240
         *         *         *         *         *         *
TACTGATAACTTGGGCGCACTATACACACGTTCCTGAAGAAAGCTATAGTTTTTTGATGGG   300
         *         *         *         *         *         *
GTTGAAGATGGCTGGATGTCTAAAATAAAACATTGCTTCATATGTTCAACTATGCGTTAAT   360
         *         *         *         *         *         *
GATTGCGTCGGTTTGAAGAACAGACGATATACGAAGTAGTTTACTAAAGCAGTTCTCATT   420
         *         *         *         *         *         *
TCAGGTGTTATTCACTTATTCCTTCTTTGAGTCTCTCCAATTAAGTACGAAGTCGTTTCT   480
```

| FIG. 18 |
|---|
| FIG. 18a |
| FIG. 18b |

FIG. 18a

```
                                          *
GTTATGCAAACCATTTATGCCGAAAGGCTCAAGTTAAGGAATGTAGA ATGTCAAATAAA 539
                                                MetSerAsnLys

*              *              *              *
ATGACTGGTTAGTAAAATGGTTAACGCTGATAAAGGTTTCGGCTTTATTCTCCTGTT 599
MetThrGlyLeuValLysTrpPheAsnAlaAspLysGlyPheGlyPheIleSerProVal

*              *              *              *
GATGGTAGTAAAGATGTGTTTGTGCATTTTCTGCGATTCAGAATGATAATTATCGAACC 659
AspGlySerLysAspValPheValHisPheSerAlaIleGlnAsnAspAsnTyrArgThr

*              *              *              *
TTATTTGAAGGTCAAAAGGTTACCTTCTCTATAGAGAGTGGTGCTAAAGGTCCTGCAGCA 719
LeuPheGluGlyGlnLysValThrPheSerIleGluSerGlyAlaLysGlyProAlaAla

*              *              *              *
GCAAATGTCATCATTACTGATTAA AATTCATCGCTCGTCTGTATACGATAACGAAGAAG 778
AlaAsnValIleIleThrAsp -

*              *              *              *
GCTGATGCCTGAGTAGAGATACGGACAGAGTAGTGAATATTGGATCTCTTTAATAAAAAG 838

*              *
TAAGGAGGTCCAATACATGAAACAATGGCTAGCATATTT 877
```

METHOD AND CONSTRUCTS FOR INHIBITING PROTEIN EXPRESSION IN BACTERIA

RELATED APPLICATIONS

This patent application is a continuation of PCT/US97/24151, filed Dec. 19, 1997, which is a continuation-in-part of U.S. application Ser. No. 08/769,945, filed Dec. 19, 1996 entitled METHOD AND CONSTRUCTS FOR INHIBITING PROTEIN EXPRESSION IN BACTERIA, now U.S. Pat. No. 5,981,280, which is incorporated herein in its entirety by reference, which application is a continuation-in-part application of application Ser. No. 60/013,922, filed Mar. 22, 1996, which was incorporated in its entirety by reference in application Ser. No. 08/769,945.

FIELD OF THE INVENTION

The invention relates to the field of biotechnology, and more particularly to the field of regulating the translation of mRNA and the production of proteins.

BACKGROUND OF THE INVENTION

Bacteria are the causative agents for a great many diseases in plants and animals, including humans. Before the advent of antibiotics, such as penicillin, bacterial infections were considered to be non-treatable. Since that time, additional antibiotics have been developed to control and kill bacteria and treat bacterial infections.

Unfortunately, however, many antibiotics have proven over time to be less and less effective at controlling bacterial populations due to the development of resistance of the bacteria to the antibiotics.

Science has responded by discovering newer and better antibiotics with which to treat resistant bacteria. As fast as new antibiotics can be produced, resistant strains of bacteria develop. Therefore, there is a clear and pressing need for new means of killing harmful bacteria.

The invention provides a novel mechanism for killing bacteria by disrupting bacterial protein production. The risk of development of bacterial resistance to the compounds and method of the invention is minimized, as compared to that encountered with traditional antibiotics, because the invention takes advantage of natural processes of the bacteria.

The invention further provides for the overproduction of the 5' untranslated region of the mRNA of a target cold shock protein. Several other novel aspects are described further herein after.

SUMMARY OF EMBODIMENTS OF THE INVENTION

It has been unexpectedly discovered that protein synthesis in bacteria can be inhibited or even completely stopped by overexpressing in the bacteria an RNA comprising a sequence which is substantially complementary to a portion of the bacterial 16S rRNA adjacent to the decoding region, which portion is known as the anti-downstream box (ADB). The RNA sequence which is substantially complementary to the ADB is referred as a downstream box (DB) because, in a naturally occurring bacterial mRNA, the DB is positioned downstream from the initiation codon of the mRNA. The structure of the 3' region of 16S rRNA and the function of the DB box as a translation initiation signal in bacteria is described in Sprengart, et al., EMBO Journal, 15(3):665–674 (1996), which is incorporated herein by reference.

The invention comprises several embodiments. In one embodiment, the invention is a method for arresting or inhibiting the production of bacterial proteins. The method of the invention comprises overexpressing in a bacterial cell an mRNA which comprises an initiation codon and a downstream box. The downstream box is preferably 3' to the initiation codon, with an intervening nucleotide sequence of 0 to 30 nucleotides. Alternatively, the downstream box may overlap the initiation codon. In this latter situation, any or all of the three nucleotides of the initiation codon may constitute the 5' end of the downstream box. The DB of the overexpressed mRNA is allowed to anneal to the ADB, thereby effectively binding the 16S rRNA and preventing translation of other mRNAs, ultimately preventing production of bacterial proteins.

In another embodiment, the invention is an oligonucleotide mRNA construct for the inhibition of protein synthesis in bacteria. The RNA construct has a nucleotide sequence which comprises an initiation codon and a DB sequence 3' to, or overlapping, the initiation codon. Preferably, the RNA construct is free of a site for RNA endonucleases.

In another embodiment, the invention is an oligonucleotide DNA construct, which DNA construct codes for an mRNA which comprises an initiation codon and a DB sequence 3' to, or overlapping, the initiation codon.

In a further embodiment, the invention is a vehicle for transforming a bacterial cell, which vehicle contains a DNA promoter sequence which is operably linked to a DNA sequence which codes for an mRNA which comprises an initiation codon and a DB sequence 3' to, or overlapping, the initiation codon.

A further embodiment is a bacterial cell which has been transformed with a vehicle containing a DNA promoter sequence which is operably linked to a DNA sequence which codes for an mRNA which comprises an initiation codon and a DB sequence 3' to or overlapping the initiation codon.

The invention is applicable to, and can be practiced in, all bacteria because of the existence of the 16S rRNA, which is a well-conserved sequence. Thus, the practice of the invention is not dependent on the bacteria species used, such as *E. coli*, which is used herein to illustrate the invention. See, Goodfellow and O'Donnell, Handbook of New Bacterial Systematics, Academic Press (1993); Stackebrandt and Goebel, International Journal of Systematic Bacteriology, 44(4):846–849 (1994); Durand and Gros, lFEMS Microbiology Letters, 140:193–198 (1996); and Olsen and Woese, FASEB Journal, 7:113123 (1993), each of which is incorporated herein by reference. The fact that bacteria in which the 16S rRNA is highly homologous with respect to that of *E. coli* includes mammalian pathogens such as Mycobacterium spp. and *Legionella pneumophila*, and even non-pathogen symbionts of marine animals, such as *Linga pensylvanica* and *Bathymodiolus thermophilus*, is indicative of the highly conserved nature of the 16S rRNA and the general applicability of the present invention. The conserved nature of the 16S rRNA permits identification of the ADB in a given bacteria from the nucleotide sequence of the 16S rRNA which can be found for bacteria in the GenBank database. Means of determining the nucleotide sequence of the 165 rRNA are known. See, for example, Lane et al., Proc. Natl. Acad. Sci., 82:6955–6959 (1985), and Bottger, FEMS Microbiology Letters, 65:171–176 (1989), each of which is incorporated herein by reference. The bacterial 16S rRNA contains, at its 3' end, an anti-Shine-Dalgarno region (SD) and a decoding region. The ADB is a 12 to 14 nucleotide long region close to the decoding region of 16S rRNA. Once the ADB is identified and its sequence ascertained, the constructs of the invention may be readily constructed for any particular bacteria, as may the vehicle of the invention, and the method of the invention may likewise be practiced in any bacteria.

Moreover, because of the highly conserved nature of the sequence of the 3' end region of the 16S rRNA, it is conceived that a DB which is substantially complementary to the ADB of the 16S rRNA of any one particular bacterial species will be sufficiently complementary to the ADB of the 16S rRNA of a second bacterial species to enable the method of the invention to be practiced in different species of bacteria using a DB of the same or similar sequence.

BRIEF DESCRIPTION OF THE FIGURES

FIG. 17 shows the nucleotide sequence of cspA and deduced amino acid sequence of the CspA protein. FIG. 17 is split into 3 slides (FIGS. 17a, b, and c), the arrangement for which can be seen from FIG. 17a. The three figures together make up the nucleotide sequence of cspA.

FIG. 18 shows the nucleotide sequence of cspB and deduced amino acid sequence of the CspB protein. FIG. 18 is split into 2 slides (FIGS. 18a and b), the arrangement for which can be seen from FIG. 18a. The two figures together make up the nucleotide sequence of cspB.

Figure 19B:
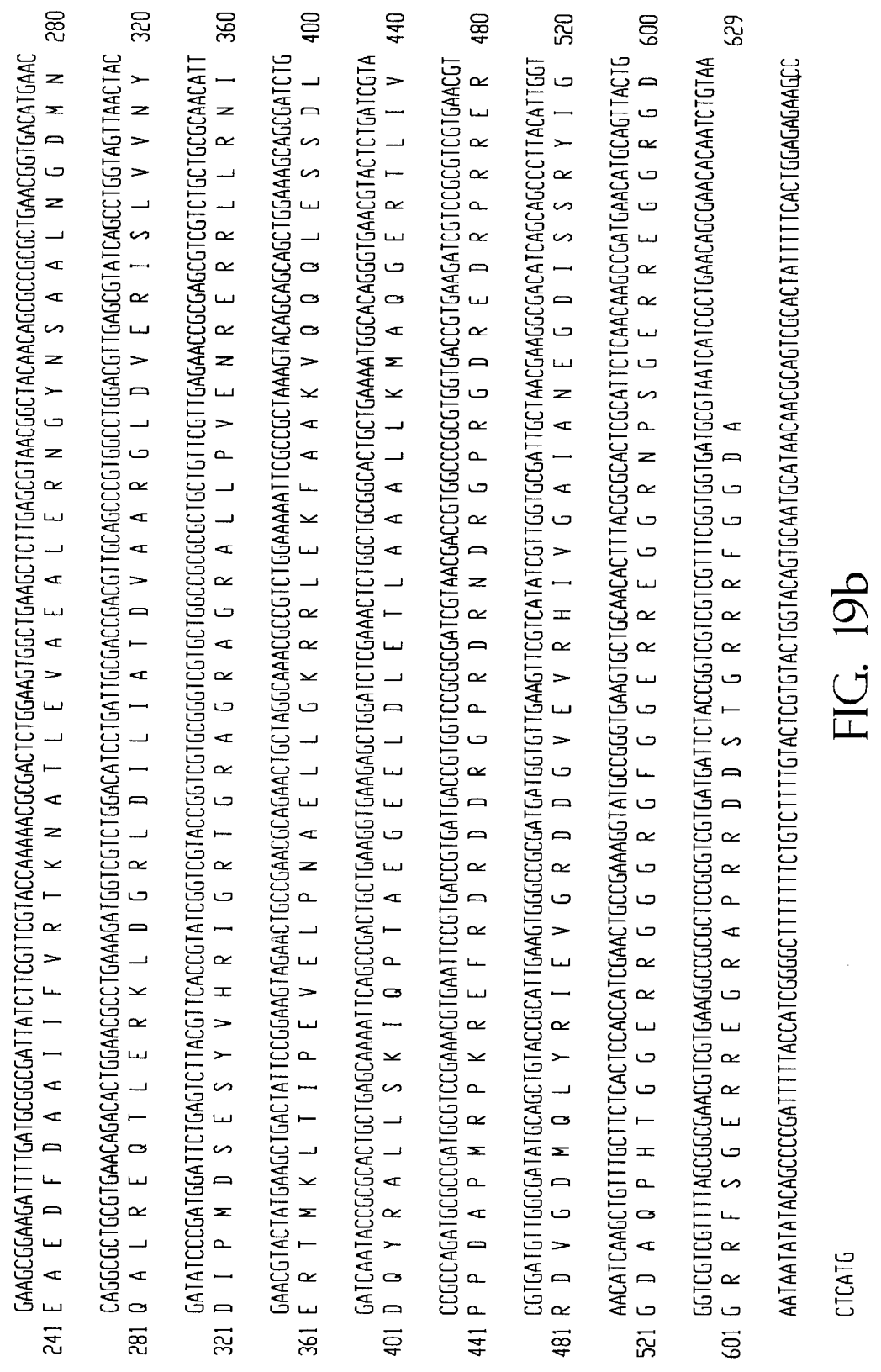

FIG. 19 shows the nucleotide sequence of csdA and deduced amino acid sequence of the CsdA protein. FIG. 19 is split into 2 slides (FIGS. 19a and b), the arrangement for which can be seen from FIG. 19a. The two figures together make up the nucleotide sequence of csdA.

DETAILED DESCRIPTION OF EMBODIMENTS OF THE INVENTION

Figure 1:
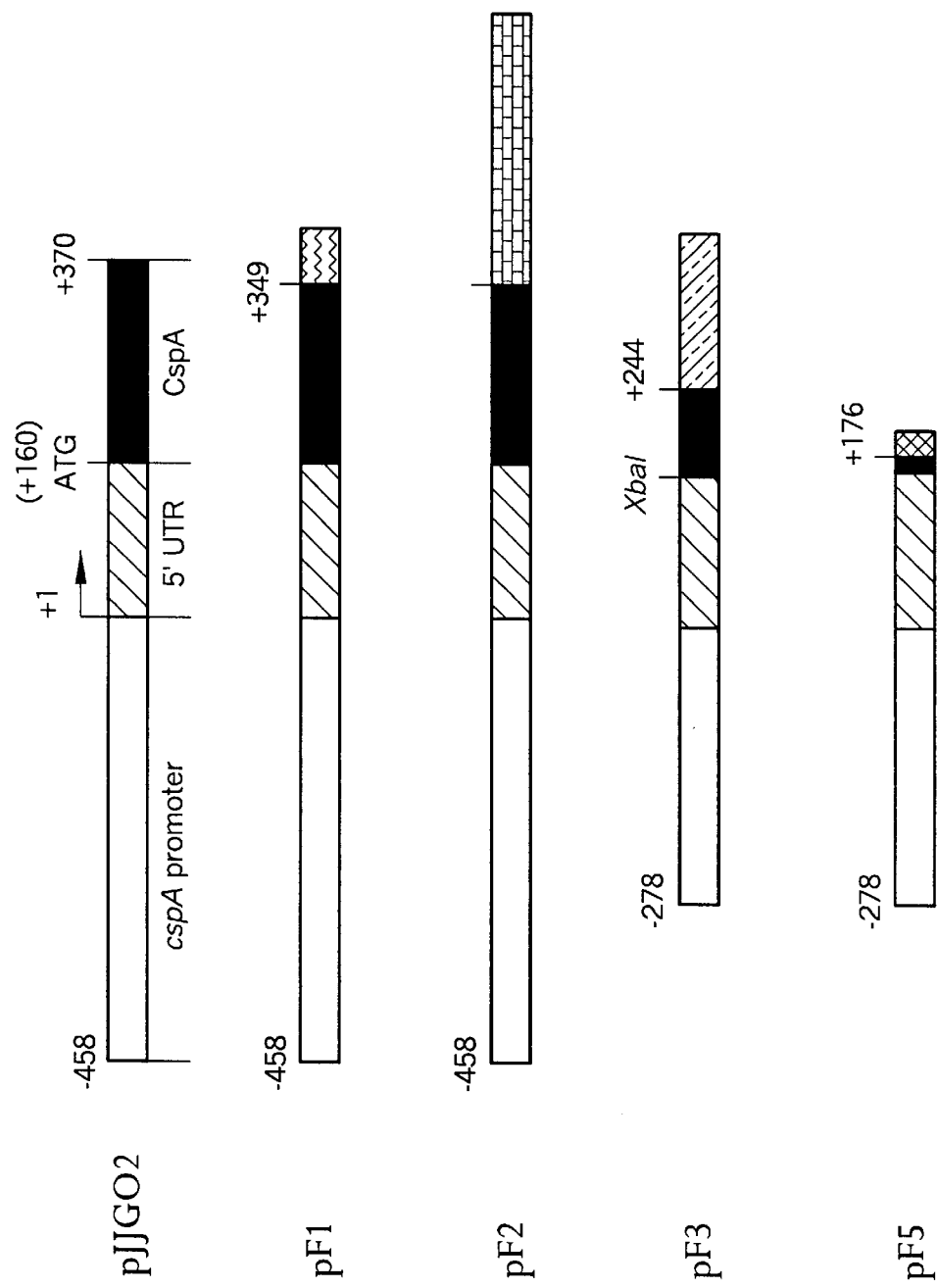
FIG. 1 shows diagrammatically the construction of DNA sequences overexpressing mRNAs of the invention.

As reported by Sprengart et al., the downstream box (DB) of bacteria plays an important role in the translation of mRNA to produce proteins. The DB binds to a portion of the bacterial 16S rRNA near the 3' end and is thought to help position the mRNA and rRNA in proper relative position for translation to occur.

In accordance with the present invention, it has been discovered that during the time when the ADB is annealed to the DB of an overexpressed mRNA, the 16S rRNA is not capable of participation in the translation of cellular mRNAs other than the annealed overexpressed mRNA. It has been further discovered that the entire protein-making machinery of a bacterium may be shut down by providing to the bacterium an mRNA, which encodes a DB which is substantially complementary to the ADB of the 16S rRNA, which anneals to all or substantially all of the bacterial 16S rRNA.

The term "complementary" as used herein, is intended to include "substantially complementary". Thus, the term "complementarity" does not require perfect complementarity. It is sufficient that the two sequences be "complementary" as defined in Kahl, Dictionary of Gene Technology, VCH Publishers, Inc. (1995), which is incorporated herein by reference. That is, two nucleotide sequences are complementary if they are capable of forming a hydrogen-bonded duplex with each other according to Watson-Crick base-pairing rules. Two complementary RNA sequences, or an RNA and a DNA sequence, will form pairings of A-U, G-C, or G-U. "Complete complementarity" is not required.

The ADB is a nucleotide sequence of about 14 bases which is positioned in the 3' end of the 16S rRNA, in close proximity to the decoding region of 16S rRNA. The 16S rRNA nucleotide sequence of known bacteria is known and can be found in the GenBank database. Thus, for a selected bacterium, the ADB can be readily identified by comparison to the sequence of the ADB in a bacterium in which the sequence is known, for example E. coli. Once the ADB is identified, a DB complementary to the ADB can be constructed, and incorporated into an appropriate mRNA, as described below.

The mRNA of the invention is an isolated mRNA or an mRNA which has been transcribed from an isolated DNA. The mRNA comprises an initiation codon, which codon is preferably AUG. Other suitable initiation codons for the mRNA include GUG and UUG.

The mRNA of the invention further comprises a downstream box sequence, which is typically 3' to the initiation codon. The codons of the DB may or may not be in phase with the initiation codon. The DB sequence may be immediately adjacent to the initiation codon so that there are no intervening nucleotides. Generally, the DB is separated from the initiation codon by an intervening nucleotide sequence between 1 and 30 nucleotides long. The base sequence of the intervening sequence is immaterial and may be constituted of any sequence of nucleotides. Preferably, the intervening nucleotide sequence is 9 to 15 nucleotides in length, with a most preferred length of 12 nucleotides. Alternatively, the DB may overlap the initiation codon. That is, any one of the three nucleotides of the initiation codon of the mRNA of the invention may form the 5' end of the DB.

The DB sequence of the mRNA of the invention is a nucleotide sequence which is complementary to the ADS of the 16S rRNA of a bacterium. Generally, the DB is between 6 and 20 bases long, preferably between 8 and 14 bases long, although the DB may be longer than 20 bases. For example, the DB may comprise nucleotides which are complementary to nucleotides 3' or 5', or both, to the ADS. Regardless of length of the DB, a higher degree of complementarity between the DB and the ADS is associated with more effective annealing, resulting in more efficient inhibition of bacterial protein synthesis, in accordance with the method of the invention.

In addition to the initiation codon, the DB, and any intervening sequence, the mRNA construct of the invention may comprise a nucleotide sequence 5' to the initiation codon or 3' to the DB. For example, the mRNA construct may comprise a sequence 3' to the DB which encodes a polypeptide or may comprise a termination codon. Likewise, the mRNA construct may comprise an untranslated sequence and/or a Shine-Dalgarno sequence 5' to the initiation codon.

The length of the mRNA construct, including the initiation codon, any intervening sequence, and DB, and exclusive of any additional nucleotides at the 5' or 3' end, may be any length between 8 nucleotides to about 45 nucleotides. Of course, if the mRNA comprises a 5' or 3' sequence in addition to the above essential components, such as a Shine Dalgarno sequence, the mRNA may be much longer, up to several hundreds of nucleotides in length.

Preferably, although not necessarily, the mRNA construct is free of sites for RNA endonucleases. It is especially preferred that the portion of the mRNA construct comprising the essential portions of the construct, that is the initiation codon and the DB, be free of sites for RNA endonucleases, which might otherwise degrade the mRNA construct and free the bacterial 16S rRNA to bind to bacterial mRNAs.

The mRNA construct of the invention may have a sequence which is similar or identical to an mRNA sequence found naturally in a bacterium. For example, the mRNAs for several cold-shock proteins, such as the mRNAs for E. coli proteins CspA, CspB, CspG, CsdA, and RbfA, comprise a Shine-Dalgarno sequence, an initiation codon, and a downstream box substantially complementary to the anti-downstream box of the E. coli 16S rRNA. Other E. coli mRNAs which contain a Shine-Dalgarno sequence, an initiation codon, and a downstream box complementary to the E. coli ADB include RecA, Hns, NusA, InfB, and CspD.

Below are several non-limiting examples of suitable DBs for the mRNA construct. Each of the following DB is substantially complementary to the ADB of the E. coli 16S rRNA which ADB has the sequence:

ADB 3' (−1481) UACUUAGUGUUUCA (−1469) 5' (SEQ ID NO:17)

DB #1: 5' AUGACUGGUAUCGU 3' (SEQ ID NO:18)

DB #2: 5' AUGACUGGUUUCGU 3' (SEQ ID NO:19)

DB #3: 5' AUGACUGGUUUAGU 3' (SEQ ID NO:20)

DB #4: 5' AUGAGUUAUGUAGA 3' (SEQ ID NO:21)

DB #5: 5' AUGGCGAAAAGAAU 3' (SEQ ID NO:22)

A suitable mRNA construct according to the invention can be constructed using any one of the above DBs, or other suitable DB, for example:

5' AUGX$_{(n)}$AUGACUGGUAUCGU 3' (SEQ ID NO:23)
where n is a whole number from 0 to 30, and X is G, C, U, or A, wherein each occurrence of X may be the same as or different from any other occurrence of X. Alternatively, the 5' end of the DB overlaps the initiation codon.

The DNA of the invention is any isolated DNA which encodes for an mRNA which is suitable for the mRNA construct of the invention, as described above. The DNA may further comprise an additional nucleotide sequence 5' to the initiation codon, which sequence may include a promoter sequence. Such promoter sequences may be used to control transcription of the mRNA construct. The DNA may comprise a sequence 5' to the initiation codon which sequence has a function other than as a promoter, such as a Shine-Dalgarno sequence, and/or a sequence which has no known function. The DNA may comprise a sequence 3' to the portion encoding the DB of the mRNA construct, which sequence may include, for example, a termination codon, or may encode a polypeptide, and a sequence required for transcription termination.

An example of a suitable DNA which encodes for the mRNA construct of the invention is:

5' ATGY$_{(n)}$ATGACTGGTATCGT 3' (SEQ ID NO:24)
where n is a whole number from 0 to 30, and Y is G, C, T, or A, wherein each occurrence of Y may be the same as or different from any other occurrence of Y. Alternatively, the 5' end of the DB overlaps the initiation codon, ATG. The DNA may contain additional sequences, as stated above, at the 5' and/or 3' end of the DNA.

The DNA sequence of the invention may be contained within a vehicle or cloning vector, such as in a plasmid or phage vector. The DNA sequence in the vector may be under the control of a promoter sequence located 5' to the initiation codon. These vectors containing the DNA of the invention may be used to transform a host bacterium which may be used to overexpress the mRNA of the invention, that is to produce the mRNA in the bacterium at levels higher than produced in similar nontransformed bacteria. Any bacterium which may be transformed by means of a cloning vector is a suitable host for the DNA sequence of the invention. Methods of producing cloning vectors and transforming bacteria are known in the art and are taught, for example, in Ausubel et al., Current Protocols in Molecular Biology, J. Wiley & Sons, Inc. (1995), which is incorporated herein by reference.

Overexpression of the mRNA sequence of the invention results in the production of the mRNA in an amount which is higher than that found normally in the bacteria. To whatever extent the mRNA is overexpressed, the production of bacterial proteins is inhibited. If the mRNA is expressed at a high enough level, production of bacterial proteins will be completely stopped, which may lead ultimately to death of the bacterium.

Therefore, the construct producing the mRNA is useful as an antibiotic to kill or to stop the growth of bacteria. The construct producing the mRNA may be packaged in a bacteriophage which would permit the mRNA to be used as a disinfectant or as a topical antibiotic preparation. It is conceivable that strategies for delivery will be devised to permit transformation of bacteria which are causing infection of a plant or animal, such as a mammal like humans, dogs, cats, cattle, horses, and livestock. Such antibiotics are safe for use in eukaryotes, as eukaryotes lack the 16S rRNA that is present in bacteria.

According to the method of the invention, an mRNA comprising an initiation codon and a DB which is complementary to the ADB of the 16S rRNA of a bacterium, is caused to be overexpressed in a bacterium, and is then allowed to anneal to the ADB of the 16S rRNA of the bacterium, thereby inhibiting production of proteins encoded by other mRNAs in the bacterium.

Any means of delivery which results in overexpression of the mRNA of the invention is suitable for the method of the invention. For example, the bacterium may be transformed by means of a vehicle harboring a DNA sequence which codes for the mRNA of the invention.

If desired, expression of the mRNA sequence of the invention is controlled by placing the DNA sequence under the control of an inducible promoter. For example, if it is desired to kill a harmful bacterium or block its growth while sparing a beneficial bacterium, the DNA sequence may be placed under the control of a promoter which is responsive to a product which is present only in the first bacterium. In this way, the lethal antibiotic effect of the mRNA of the invention will affect only the undesirable, harmful bacterium.

Another means of controlling the expression of the protein production-inhibiting mRNA sequence is to employ a DNA sequence which codes for an mRNA which is unstable under certain conditions.

For example, the 5' untranslated region (5' UTR) of the mRNA of the *E. coli* cold-shock protein, CspA, contains a region immediately 5' to the Shine-Dalgarno region which is susceptible to degradation, presumably by RNAase E, at physiologic growth temperatures of about 37° C. Therefore, the cspA mRNA containing the 5' UTR is unstable under normal growth conditions, having a half life estimated to be approximately 12 seconds. Other cold-shock proteins, such as *E. coli* CspB and CsdA, are similarly unstable at physiologic growth temperatures due to instability of their mRNA. Upon cold shock, such as when the temperature is reduced to 15° C., the half life of the cspA mRNA increases dramatically, to about 15 minutes, an increase in stability of about 75 times over the mRNA at normal physiologic growth temperatures.

Because of the instability at 37° C. of an mRNA containing the 5' UTR of cspA mRNA, this region, or the 5' UTR of the cspB or csdA mRNA, can be used to control the expression of the mRNA sequence of the invention, so that its antibiotic effect occurs only below physiologic growth temperatures, such as under cold-shock conditions. The antibiotic effect of the method of the invention is augmented at cold-shock conditions because a cold-shocked bacterium requires new ribosomal factors, whose synthesis is blocked by overproduction of an mRNA containing the DB sequence.

The antibiotic effect of the method of the invention in which the mRNA of the invention is caused to be overexpressed within a bacterium is increased concomitantly with an increase in copy number of the mRNA which is to be expressed. That is, whereas a minimal overexpression of the mRNA of the invention will inhibit the production of proteins by the bacterium, such an inhibition may not be sufficient to prevent further growth of the bacterium or to kill the bacterium. Higher levels of expression of the mRNA result are positively correlated with increased inhibition of protein production. When the copy number is sufficiently high in the bacterium, protein production will be completely blocked.

A similar effect is noted with respect to complementarity of the DB of the overexpressed mRNA and the ADB of the bacterial 16S rRNA. Overexpression of an mRNA comprising a DB with 100% complementarity will be more efficient in binding to the ADB than will be an mRNA comprising a DB with lesser, say 75% complementarity. Thus, the protein blocking effect of an mRNA having a more highly complementary DB will be more pronounced compared to that of an mRNA having a less complementary DB. Therefore, when using an mRNA having a less complementary DB, it may be necessary to express the mRNA in a higher copy number to achieve the same or similar antibiotic results as with an mRNA having a more complementary DB.

The translational inhibitory properties of the downstream box are also advantageous for overexpressing a heterologous gene in a transformed bacterium after cold shock. Inhibition of the translation of endogenous bacterial proteins will allow the heterologous gene product to accumulate to very high levels in the transformed organism. Furthermore, a construct containing the downstream box in conjunction with a strong promoter and the 5' untranslated region of a cold shock inducible gene, which functions to stablize the mRNA transcript at reduced temperature, will direct efficient high level expression of the heterologous gene at reduced temperature.

SUMMARY OF FURTHER EMBODIMENTS OF THE INVENTION

A further important embodiment of the invention relates to the role of the 5'-end untranslated region of the mRNA for cspA, the major cold-shock protein of *Escherichia coli*, in cold-shock adaptation.

BACKGROUND OF THE INVENTION

Another important embodiment of the invention relates to the role of the 5'-end untranslated region of the mRNA for cspA, the major cold-shock protein of *Escherichia coli*, in cold shock adaption. However, the scope of the invention is not limited solely to the adaptation of a bacterium to cold-shock, but to any environmental or growth condition that results in physiologic stress that elicits the cold shock response (e.g., the expression of the polypeptides encoded by the cold shock genes) of a bacterium. For example, exposing a bacterium to environmental or growth conditions outside of the normal physiologic condition for that organism will bring such a response.

When the culture temperature of exponentially growing *Escherichia coli* cells are shifted from 37 to 10° C., there is a growth lag period before reinitiation of cell growth (Jones et al. 1987). Similar to the heat-shock response, *E. coli* responds to the temperature downshift by inducing a specific pattern of gene expression called cold-shock response, which includes induction of a set of proteins defined as cold-shock proteins (Jones et al. 1992; for review, see Jones and Inouye 1994). The cold-shock response occurs during the lag period of cell growth, and is considered to be required for cellular adaptation to low temperature.

CspA, the major cold-shock protein in *E. coli*, is dramatically induced upon temperature downshift, whose production reaches as high as 13% of total protein synthesis (Goldstein et al. 1190). Interestingly, however, CspA production during cold-shock response is transient and drops to a basal level at the time of reinitiation of cell growth at low temperature. CspA consists of 70 amino acid residues, and shows 43% identity to the "cold-shock domain" of the eukaryotic Y-box protein family which is known to be associated with gene regulation and mRNA masking (for review, see Wolffe et al. 1992; Wolffe 1993). The three-dimensional structure of CspA has been determined, consisting of five anti-parallel β-sheets which form a β-barrel structure (Newkirk et al. 1994; Schindelin et al. 1994). Two RNA binding motifs, RNP1 and RNP2, are identified on B2 and B3 sheets, respectively. In the structure, seven out of eight aromatic residues are located on the same surface and a single-stranded DNA was shown to interact with these surface aromatic residues (Newkirk et al. 1994). It has been proposed that CspA function as an RNA chaperone to facilitate translation efficiency at low temperature (for review, see Jones and Inouye 1994).

*E. coli* contains a large CspA family, including CspB, CspC, CspD, and CspE (Lee et al. 1994; Dongier et al. 1992; Yamanaka et al. 1994). Among them, only CspA and CspB have been shown to be cold-shock inducible (Lee et al. 1994). Recently, another cold-shock protein, CsdA was identified which is exclusively associated with ribosomes and has ability to unwind double-stranded RNA (Jones et al. 1995).

SUMMARY OF THIS EMBODIMENT OF THE INVENTION

During cellular adaptation to low temperature, *Escherichia coli* transiently synthesizes the major cold-shock protein CspA. In accordance with the invention, it was found that the adaptive process to cold shock is blocked when the 143-base sequence of the 5' untranslated region of the cspA mRNA was overproduced. The overproduction of this untranslated region at 15° C. caused the synthesis of not only CspA but also other cold-shock proteins such as CspB and CsdA to be no longer transient but rather prolonged expression. In addition, inhibition of both the synthesis of cellular proteins other than cold-shock proteins and cell growth was observed. Interestingly, when CspA was also overproduced together with the 5' untranslated region, normal cold-shock adaptive response was resumed without a prolonged lag period of cell growth. This indicates that the 5' untranslated region of the cspA mRNA as well as its gene product CspA play a critical role in the regulation of the expression of cold-shock genes and cold-shock adaptation. Sequence similarities were found in the 5' untranslated regions of cspA, cspB and csdA mRNAs. In accordance with the invention, it is proposed that a putative repressor binds to the common sequence (cold-box) of the cold-shock mRNAs during the adaptive process, which in turn blocks the transcription of the cold-shock genes. CspA appears to promote either directly or indirectly the repressor function.

In accordance with the invention, it is demonstrated that overproduction of the 5' untranslated region of the cspA mRNA upon cold-shock results in the prolonged inhibition of the synthesis of cellular proteins as well as a prolonged lag period of cell growth. Concomitantly, the synthesis of cold-shock proteins, such as CspA, CspB, and CsdA, was no longer transient but rather persisted for a longer time which corresponds to the prolonged lag period of cell growth. Sequence similarities were found within 5' end untranslated region of mRNAs for cspA, cspB, and csdA. Interestingly, when cspA was overproduced together with the 5' untranslated region of its mRNA, the normal cold-shock response was resumed without a prolonged lag period. These results indicate that cold-shock genes are regulated by a novel mechanism during the cold-shock response. A putative repressor is proposed to bind to the common sequence (cold box) within the regions of cold-shock mRNAs, which in turn blocks the transcription of these genes. Thus, further proposed that CsaA directly or indirectly promotes the repressor function.

The invention is illustrated by the following non-limiting examples.

EXAMPLE 1

*E. coli* Strain and Culture Media

*E. coli* CL83 [recA ara (lac-proAB) rpsL(=strA) φ80 lacZ M15] (Lerner and Inouye, Nuc. Acids Res., 18:4631 (1990)) was used for all experiments and was grown in M9-Casamino acids medium (Miller, J H, Experiments in Molecular Genetics, Cold Spring Harbor Laboratory, Cold Spring Harbor, N.Y. (1972)). For pulse-labeling experiments, a complete amino acid mixture except for methionine was used. The final concentration of each amino acid was 50 µg/ml. Pulse-labeling experiments and SDS-polyacrylamide gel electrophoresis (SDS-PAGE) were carried out as described in Jiang et al., J. Bacteriol., 175:5824–5828 (1993), incorporated herein by reference.

EXAMPLE 2

Plasmid Constructions

The following plasmid constructions are shown diagrammatically in FIG. 1.

Plasmid pF1 was constructed as follows: pJJG02 (Goldstein et al., P.N.A.S., 87:283–287 (1990)) which contains the wild type cspA was digested by PvuII. The released 898-bp fragment contains the cspA gene from −458 to +348 bp (as the transcription initiation site is defined +1) which includes the entire cspA promoter, the 5' untranslated region including the Shine-Dalgarno region, and the cspA sequence for N-terminal 63 amino acid residues. Subsequently, this fragment was recloned into pUC19 digested with PvuII As a result, the CspA N-terminal 63-residue sequence was fused with a 19-residue sequence from lacZ sequence which was resulted from +1 frame shift on lacZ at base 308 pUC19 sequence (Yanisch-Perron et al., Gene, 33:103 (1985)).

pF2 was constructed in a similar way as that of pF1, except that the 898-bp fragment was recloned into the SmaI site of pUC19 instead of PvuII. As a result, the CspA N-terminal 63-residue sequence was fused with an 89-residue sequence from lacZ in the same reading frame from base 411 to 149 of pUC19.

pF3 was constructed as follows: a truncated cspA fragment (−280 to +243) was PCR-amplified from pJJG21 which was constructed from pJJG02 by creating an XbaI site at the SD sequence of cspA as follows: 5'-AATT<u>T</u>(A)<u>C</u>(T)TA<u>G</u>(A)AGGTAA-3' (SEQ ID NO:25) (the original nucleotides in the parenthesis were substituted by the underlined nucleotides). The two primers for PCR were primer 3552 (5'-GACAGGATTAAAAATCGATG-3') (SEQ ID NO:26) and 3551 (5' TTTAGAGCCATCGTCAGGAG-3') (SEQ ID NO:27). The fragment was cloned into the SmaI site of pUC19. As a result, the N-terminal 28-residue sequence of CspA was fused with a 54-residue sequence from lacZ which was resulted from +1 frame shift at base 414 of pUC19.

pF5 was constructed as a frameshift mutation by two-step PCR. In the first step, PCR was carried out with primer 3552 and primer 6879 [5'-ACGATACCAGTCGATT TTACCGGAC-3'] (SEQ ID NO:28). In the second step, PCR was carried out using PCR1 product and 4860 [5'-CTGTCGACTTACTTACGGCGTTGC-3'] (SEQ ID NO:29) as primers. pJJG02 was used as the template for both PCR reactions. The resulting PCR product which has a C residue inserted at the second position of the fifth-codon of cspA, was then cloned into the SmaI site of pUC9. All the fusion constructs described above were confirmed by sequencing (Sanger et al., P.N.A.S., 74:5463–5467 (1977)).

pF2A was constructed as follows: a HindIII/SmaI fragment which contains the entire cspA gene was obtained from pJJG02 and cloned into pF2 digested with HindIII/HincII. Thus, the orientation of cspA is opposite to that of the fusion gene.

pF2B was constructed as follows a 2.1 kb HindIII fragment which contains the entire cspB gene was obtained from pSJ7 (Lee et al., Mol. Microbiol., 11:833–839 (1994)) and cloned into pF2 digested with HindIII. The orientation of cspB is opposite to that of the fusion gene.

EXAMPLE 3

Inhibition of Cellular Protein Synthesis by Cold-shock Induction of mRNA of the Invention

Figure 2:
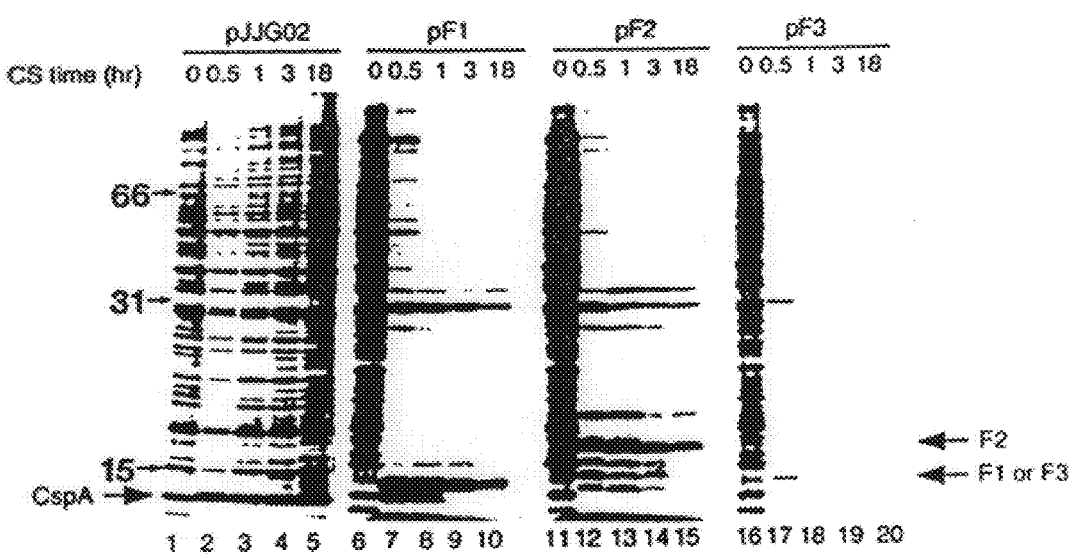
FIG. 2 shows inhibition of cellular protein synthesis by overexpression of the mRNA of the invention.

*E. coli* cell CL83 transformed with different DNA constructs as described in Example 2 were pulse-labeled for 15 mm with [$^{35}$S] methionine at 0, 0.5, 1, 3 and 18 hr after temperature downshift to 15° C. as described previously (Jiang et al. (1993)). The DNA constructs and the time points of labeling are indicated on the top of each lane. The protein synthesis pattern was analyzed by 17.5% SDS-PAGE, as shown in FIG. 2. The cell extract from a 0.25-ml cell culture was loaded. A: Lanes 1 to 5, cells with pJJG02; lanes 6 to 10, cells with pF1; lanes 11 to 15, cells with pF2; lanes 16 to 20, cells with pF3. The positions of CspA and the fusion proteins F1, F2, and F3 are indicated by the arrows. The positions of molecular weight markers (kDa) are shown at the righthand side. B: Lanes 1 to 4, cells with pUC19; lanes 9 to 12, cells with pF5.

*E. coli* CL83 was transformed with the plasmids for the CspA fusion proteins and the production of cellular proteins was examined using [$^{35}$S]methionine after temperature downshift from 37 to 15° C. Total cellular proteins were then analyzed by SDS-PAGE as shown in FIG. 2. Cells carrying pJJG02 with the intact cspA gene produced little CspA if any at 37° C. (lane 1, while upon cold-shock CspA production was dramatically induced (lanes 2 and 3). It should be noticed that the production of total cellular proteins was significantly reduced at 30 min in contrast to a high level of CspA expression (lane 2). This is a typical cellular response during cold-shock adaptation. Cells recovered from growth inhibition after a few hours and cellular protein synthesis returned to full activity after 3 hr (lanes 4 and 5). Because pJJG02 is a multicopy plasmid carrying the intact cspA gene, CspA production was not reduced to a low basal level, even after 18 hr of cold shock, which usually occurs in normal cells.

For cells harboring three different cspA fusion constructs, the synthesis of cellular proteins at 37° C. was similar to that of pJJG02 (compare lanes 6, 11, and 16 with lane 1, FIG. 2). Upon temperature downshift, all three fusion proteins (F1, F2, and F3) were cold-induced as indicated by arrows. Surprisingly, the synthesis of almost all cellular proteins was severely inhibited throughout all time points examined at 15° C. (lanes 7 to 10, lanes 12 to 15, and lanes 17 to 20 for F1, F2, and F3, respectively), indicating that the cells were no longer capable of cold-shock adaptation. Besides the CspA fusion proteins, there is a major band in the middle of the gel, which was identified as β-lactamase, the product of the ampicillin-resistant gene (bla) in the plasmid used. These results indicate that the CspA fusion protein and the protein which is encoded downstream of the CspA fusion protein gene on the plasmid were synthesized successfully in contrast to the synthesis of the cellular proteins which was severely inhibited.

EXAMPLE 4

Inhibition of Cell Growth at Low Temperature

Figure 3:
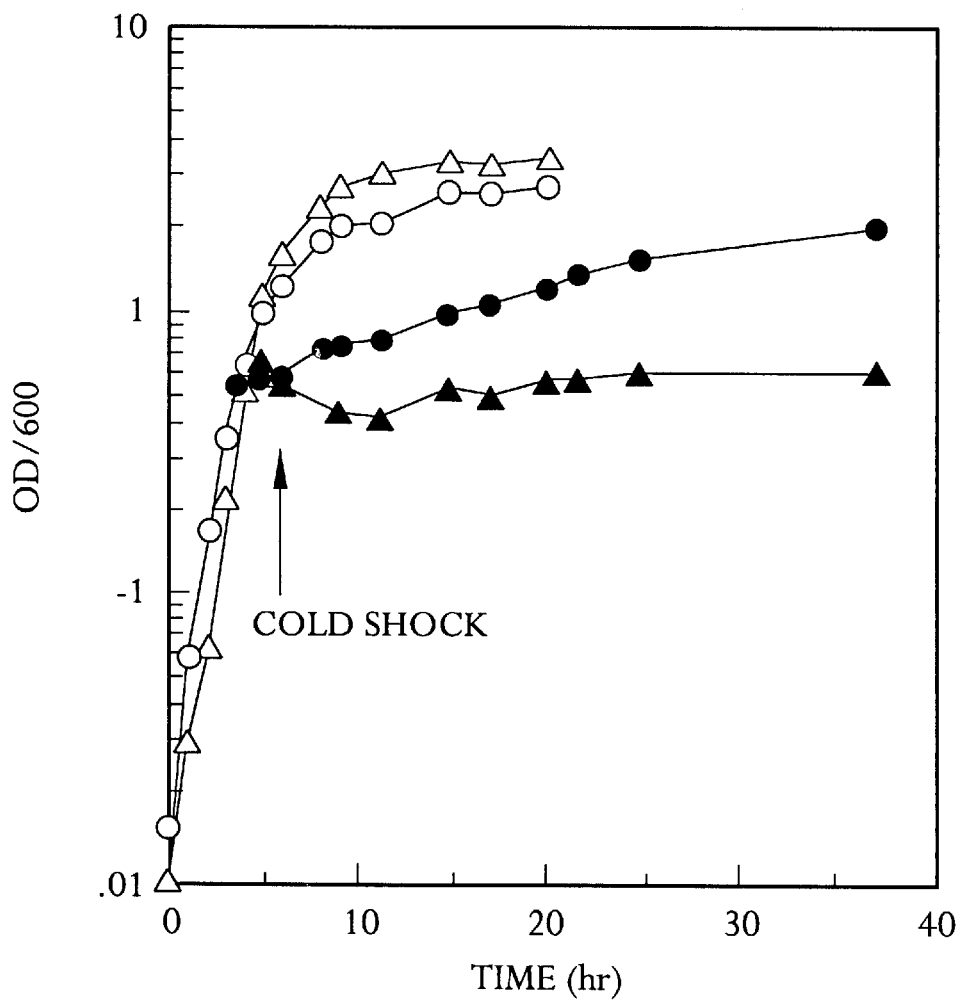
FIG. 3 shows inhibition of cell growth at low temperature due to cold-shock induced expression of the mRNA of the invention.

As shown in FIG. 3, CL83 cells transformed with pJJG02 or pF2 were grown at 37° C. in M9-Casamino acid medium. At mid-log phase ($OD_{600}$=0.6), the cell culture was divided into two. One was kept at 37° C., while the other was shifted to 15° C. Cell densities were measured at $OD_{600}$ by a Perkin-Elmer Spectrometer. pJJG02: ○ - - - ○, 37° C.; · - - - ·, 15° C. pF2: Δ - - - Δ, 37° C. ▼ - - - ▼, 15° C. Cells transformed with pF1 or pF3 behavior as did the cells transformed with pF2.

EXAMPLE 5

Figure 4:
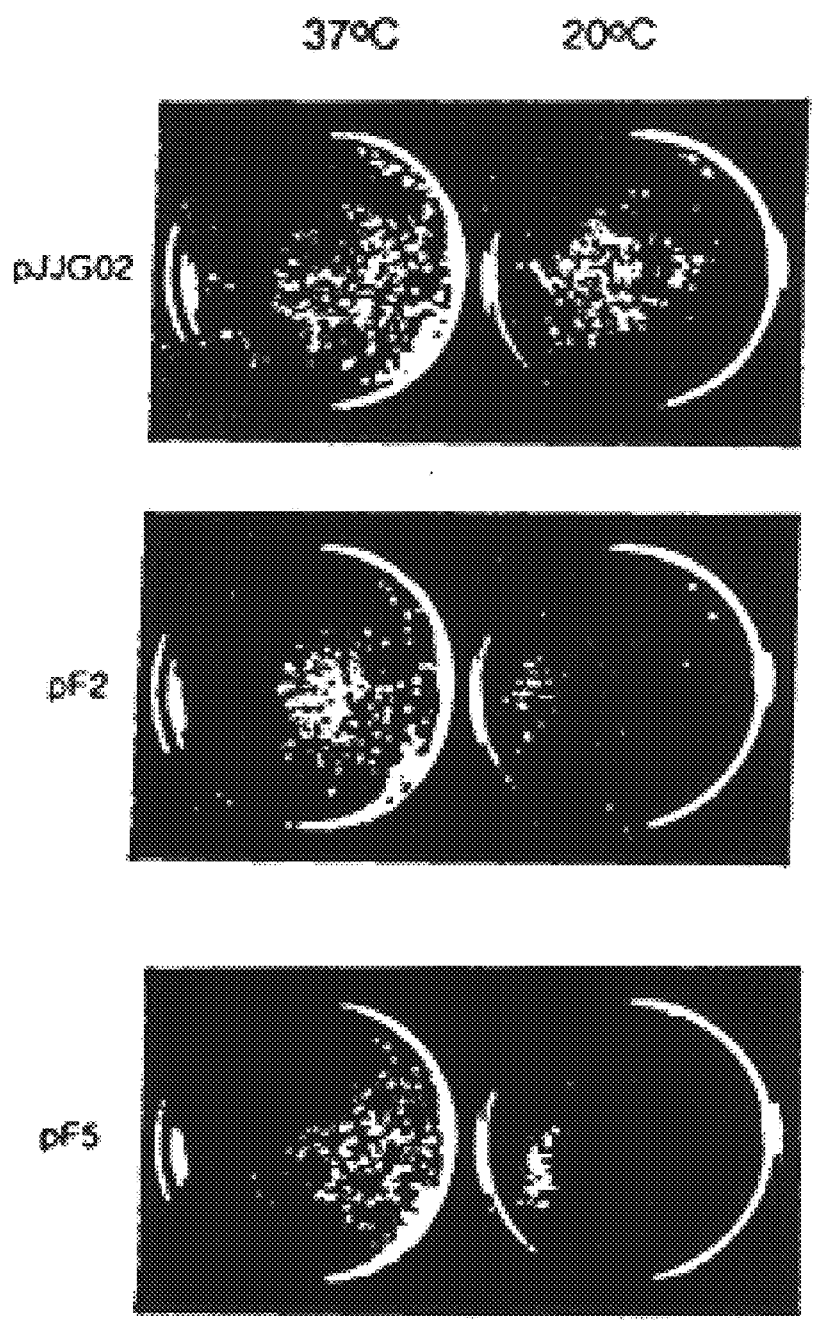
FIG. 4 shows the inhibitory effect of overexpression of the mRNA of the invention on bacterial colony formation.

Effect of Overexpression of the mRNA of the Invention on Bacterial Colony Formation CL83 cells harboring the different plasmids were grown in L-broth medium supplemented with ampicillin (50 μg/ml) at 37° C. At mid-log phase, cells were plated on two L-broth agar plates with ampicillin (50 μg/ml). One plate was incubated at 37° C. for 12 hr and the other at 20° C. for 36 hr. FIG. 4 shows inhibition at cold-shock temperature of colony growth of bacteria harboring plasmids pF2 or pF5. Growth of bacteria harboring plasmids pF1 or pF3 was likewise inhibited.

EXAMPLE 6

Figures 5A, 5B:
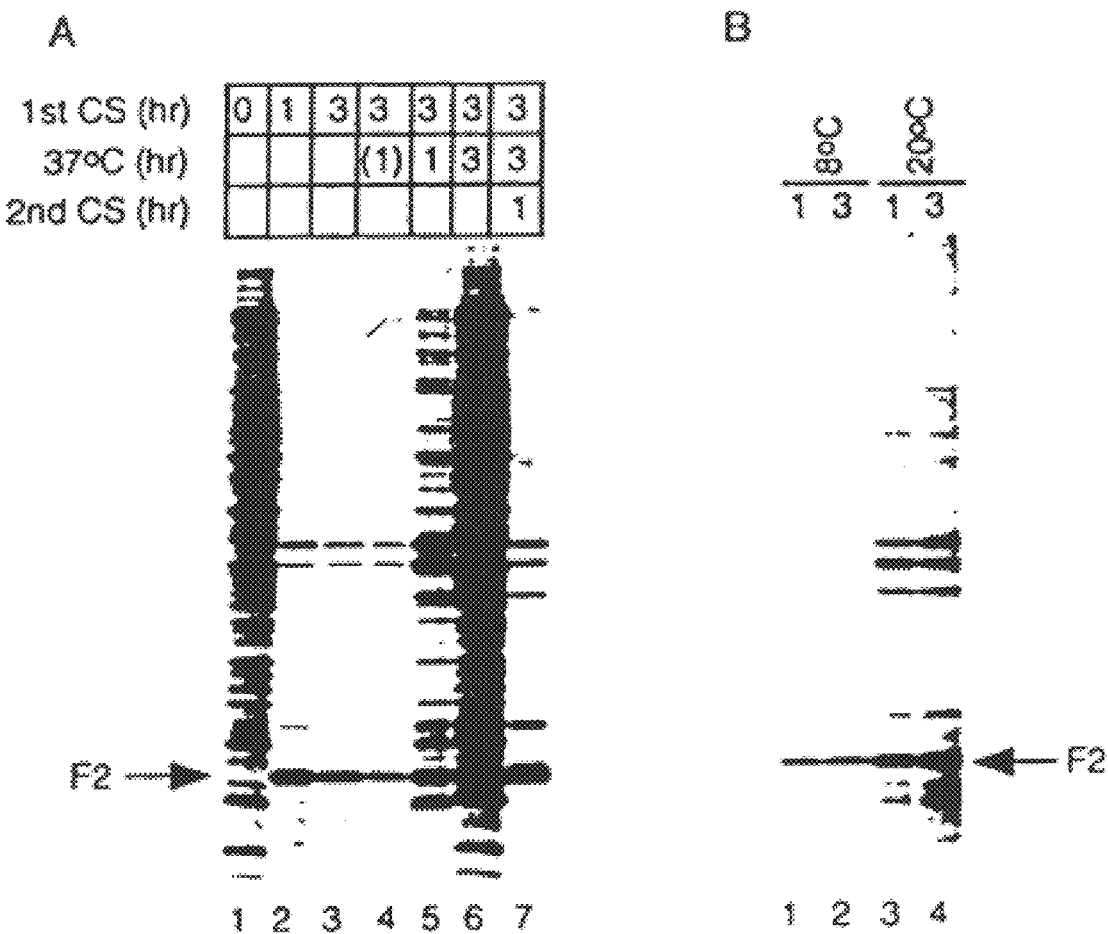
FIG. 5a shows the expression of bacterial protein production due to expression of the mRNA of the invention.
FIG. 5b shows the blocking of protein synthesis in CL83 cell shifted from 37 to 15 ° C.

Low Temperature Expression of the mRNA of the Invention Suppresses Bacterial Protein Production When CL83 cells harboring pF2 were shifted from 37 to 15° C., F2 production was dramatically induced and cellular protein synthesis was almost completely blocked (FIG. 5B, lanes 2 and 3) When cells were first labeled at 3 hr at 15° C. followed by chasing the labeled production for another 1 hr at 37° C., the F2 band can still be detected (lane 4), indicating that F2 is quite stable at 37° C. In another experiment, after the cells were first cold-shock treated for 3 hr at 15° C., the culture was shifted back to 37° C., and after 1 hr incubation at 37° C., cells were pulse-labeled. As shown in lane 5, the synthesis of cellular proteins was mostly recovered and F2 was still produced at a relatively high level. This result demonstrates that the expression at 37° C. of a DNA encoding the mRNA of the invention, at which temperature the mRNA is unstable, had no inhibitory effects on cellular protein synthesis. If pulse-labeled at 3 hr after shifting back to 37° C., no more F2 was synthesized and cellular protein synthesis was completely restored (lane 6). In order to confirm the cells still harbored the pF2 plasmid, the cells were shifted back to 15° C. for the second time, again F2 production was induced and the cellular protein synthesis was blocked (lane 7). These results demonstrate that the inhibitory effects by the expression of the DNA encoding the mRNA are exerted only at low temperatures, under the conditions used.

EXAMPLE 7

Figure 6:
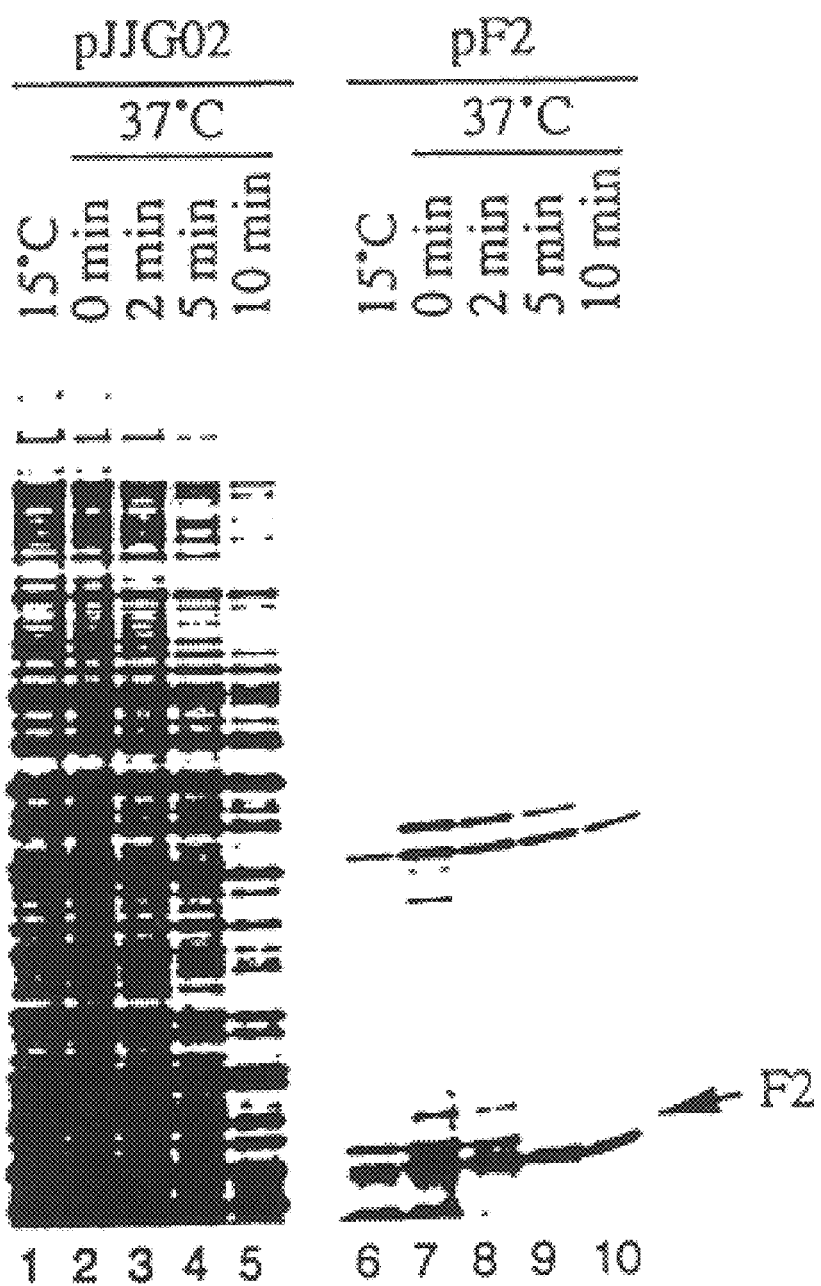
FIG. 6 shows the translation of endogenous mRNAs from cells overexpressing the exogenous mRNA of the invention.

Translation of Endogenous mRNAs from Cells Overexpressing the mRNA of the Invention Cells carrying pF2 were first cold-shock treated for 3 hr at 15° C. Rifampicin (200 µg/ml) was then added to the culture, and after 10 min incubation the culture was shifted back to 37° C. The cells were then pulse-labeled with [$^{35}$S]methionine for 5 min at 0 (lane 7, FIG. 6), 2 (lane 8), 5 (lane 9) and 10 min (lane 10) after the temperature shift. A similar labeling experiment was carried out as a control with the cells harboring pJJG02 (lanes 1 to 5, FIG. 6). As shown in lane 1, the control cells were well adapted to 15° C. after 3 hr incubation producing all cellular proteins, while cells with pF2 were strongly inhibited from producing bacterial proteins, producing mainly the F2 fusion protein and β-lactamase (lane 6). After the addition of rifampicin, very similar patterns of protein synthesis to that at 15° C. (compare lanes 2 to 5 with lane 1) were obtained for the cells with pJJG02, indicating that the same mRNAs were used before and after the addition of rifampicin. In the case of cells with pF2, major proteins produced at 37° C. after the addition of rifampicin (lanes 7–10) were identical to those produced by the translation inhibited cells (lane 6), indicating that except the mRNAs used for translation in the translation inhibited cells, no other cellular mRNAs existed in the cells. These results indicate that almost all polysomes in the cells in which translation of bacterial mRNAs was inhibited by the method of the invention were occupied with the mRNA of the invention.

EXAMPLE 8

Figure 7A:
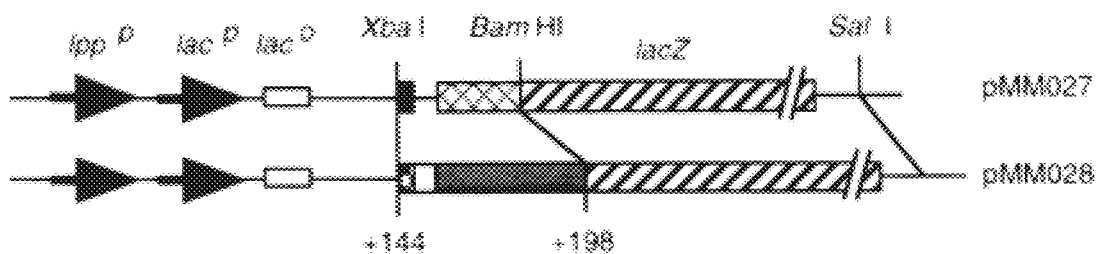
FIG. 7a shows two β-galactosidase expression systems, pMM027 and pMM028, each fused to lacZ.

Protein Production with Bacterium Transformed with a Gene Encoding a Downstream Box In order to directly compare the translational efficiency of the translation initiation regions of cspA and lpp, two β-galactosidase expression systems, pMM027 and pMM028, were constructed in such a way that each translation initiation region was placed under the same promoter and fused to lacZ (FIG. 7a). pMM027 was constructed by inserting the promoterless lacZ from pKM005 at the downstream of the lpp promoter, one of the strongest promoters at 37° C. in E. coli, and the lac promoter-operator region from a pINIII plasmid (Inouye, 1983). In pMM028, the translation initiation region of pMM027 was replaced by the fragment from +144 to +198 of cspA. In order to insert this fragment, an XbaI site was introduced immediately upstream of the putative SD sequence of cspA and the sequence around the SD sequence was changed from (+143) TATTAAGG (+150) to TCTAGAGG, where the SD sequences were underlined. The lacZ genes in both constructs were identical, which were translationally fused to the upstream region at the BamHI site. In pMM027, the initiation codon and the second residue, Lys, were derived from lpp and 8 more residues (GGIPSLDP) (SEQ ID NO:30) were added to fuse to lacZ at the 8th amino acid residue; while in pMM028, the region from the initiation codon to the 13th residue derived from CspA, plus three residues (LDP) resulted from the creation of a BamHI site, were translationally fused to lacZ at the 8th amino acid residue.

Figure 7B:
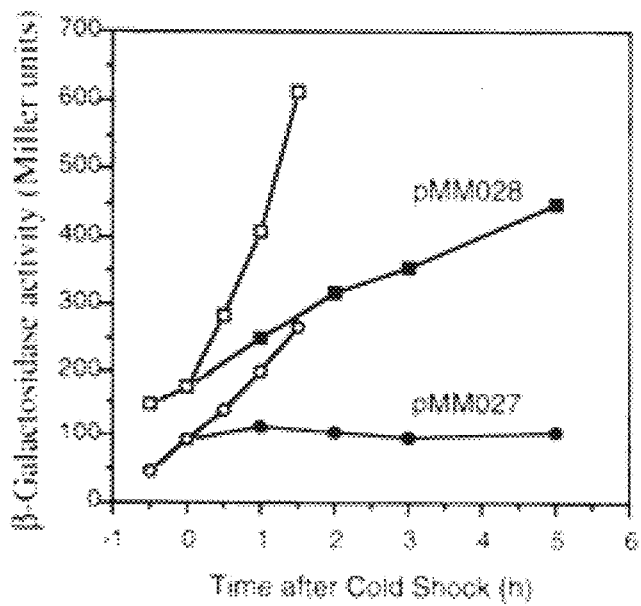
FIG. 7b shows the β-galactosidase activity vs. time after cold-shock for pMM028 and pMM027.

Both pMM027 and pMM028 contained the identical promoter. The transcripts from these constructs were also identical, except for the short region from the SD sequence to the translational fusion site; MKGGIPS (SEQ ID NO:31) for pMM027 and MSGKMTGIVKWFN (SEQ ID NO:32) for pMM028, followed by lacZ. Cells harboring these plasmids were grown in M9-Casamino acid medium at 37° C. and at mid-log phase, isopropyl-β-D-galactopyranoside (IPTG) was added to a final concentration of 1 mM. At 30 min after the addition of IPTG, the culture was divided into two; one was kept at 37° C. and the other shifted to 15° C. β-galactosidase activity for both cultures at 37° C. was steadily induced as shown in FIG. 7b. However, after temperature downshift, there was no increase of β-galactosidase activity for cells harboring pMM027, while β-galactosidase activity steadily increased at 15° C. for cells harboring pMM028.

EXAMPLE 9

Requirement of the Down-stream Box for Cold-shock Induction

Figure 8A:
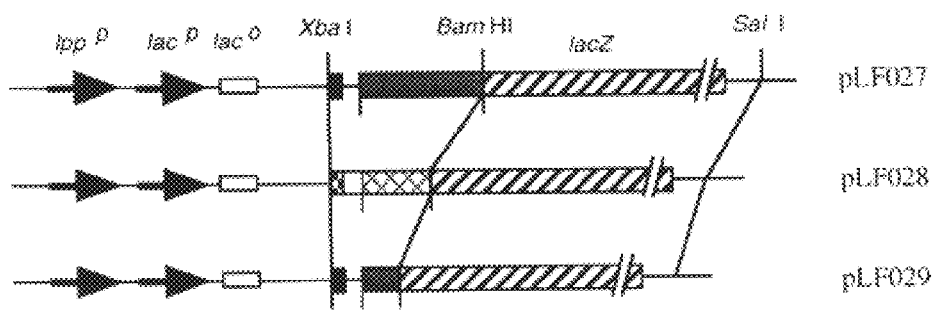
FIG. 8a shows the construction of pLF027, pLF028, and pLF029 galactosidase expression systems.

In order to elucidate the exact region responsible for the cold-shock induction of the lacZ gene, we next exchanged only the coding sequences between pMM027 and pMM028 to construct pLF027 and pLF028. pLF027 was identical to pMM027, except that the N-terminal 7-residue sequence (MKGGIPS) (SEQ ID NO:31) corresponding to the sequence between the initiation codon and the lacZ fusion site of pMM027 was replaced with the N-terminal 13-residue sequence (MSGKMTGIVKWFN) (SEQ ID NO:32), corresponding to the sequence between the initiation codon and the lacZ fusion site of pMM028 (see FIG. 8a). Similarly, pLF028 was identical to pMM028, except that the N-terminal 13-residue sequence of pMM028 was replaced with the N-terminal 7-residue sequence of pMM027 (see above). pLF027 was constructed as follows: PCR was carried out with primer #7485, 5'-cg tctagaGGGTATTAATAATGTCCGGTAAAATGAC-3' (SEQ ID NO:33), and primer M13–47, 5'-CGCCAGGGTTTTCCCAGTCACGAC-3' (SEQ ID NO:34) using pMM028 as template. The PCR product was first digested with BamHI and XbaI, and cloned into pMM027 digested with XbaI and BamHI.

pLF028 was constructed in the same way as pLF027 except that in the PCR reaction primer #7486 5'-cg ctcagaGGTAATACACTATGAAAGGGGGAATTCC-3' (SEQ ID NO:35) was used in place of primer #7485.

pLF029 was constructed as follows: oligonucleotide #7493, 5'-CTAGAGGTAATACACTATGTCCGGTAAG-3' (SEQ ID NO:37) were first annealed and then cloned into pMM027 digested with XbaI and BamHI. The DNA sequences of all the constructs were confirmed by DNA sequencing using the chain-termination method (Sanger et al, 1977).

E. coli AR137 was transformed with pLF027 and pLF028, and β-galactosidase activity was measured in the presence of lmM IPTG. At 37° C. β-galactosidase was induced almost identically in the cells harboring activity hardly increased in the cells harboring pLF028 at 15° C. In contrast, β-galactosidase activity steadily increased in the cells harboring pLF027 at 15° C. (FIG. 8b) These results, together with pMM027 and pMM028 show that a short coding sequence at the N-terminal region, but not the region upstream of the initiation codon including the SD sequence, was responsible for the translation efficiency of the lacZ fusion mRNA at 15° C. The mRNA from pLF027 has high translational efficiency, while the mRNA from pLF028 does not.

Figure 8B:
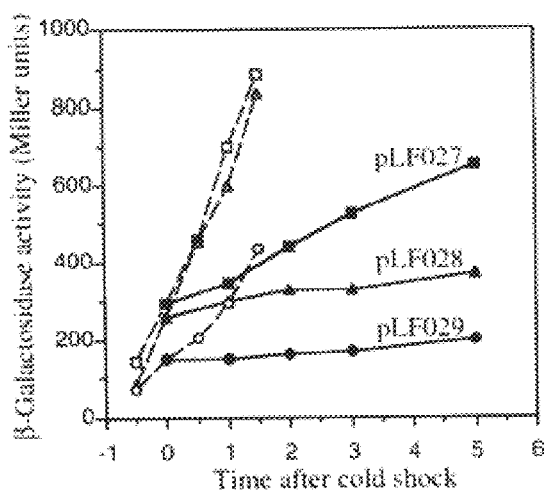
FIG. 8b shows the β-galactosidase activity vs. time after cold-shock for pLF027, pLF028, and pLF029 galactosidase expression systems.
Figure 8C:
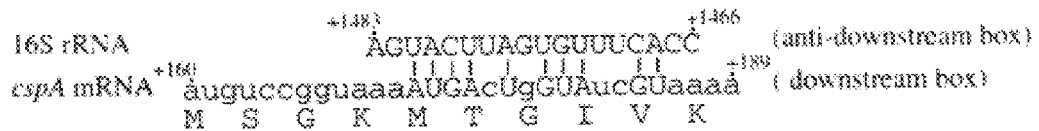
FIG. 8c shows the 16SrRNA anti-downstream box and the correspondence to cspA mRNA downstream box.

In order to examine if the downstream box sequence was responsible for the efficient translation of the transcript from pLF027 at 15° C., the lacZ gene was fused at the 4th codon of cspA to delete the downstream box sequence, yielding pLF029 (see FIG. 8a for the construction and FIG. 9C for the DNA sequence). E. coli AR137 transformed with pLF029 was examined for the induction of β-galactosidase activity at 37 and 15° C., as described for pLF027 and pLF028. As shown in FIG. 8b, the β-galactosidase activity at 37° C. was approximately 50% of that with pLF027, indicating that the translation efficiency of the pLF027 mRNA at 37° C. was regulated by both the SD sequence and the downstream sequence. However, in contrast to the pLF027 mRNA, there was no increase of β-galactosidase activity upon cold shock. This result clearly demonstrated that the downstream box sequence played a major role in the efficient translation of the cspA mRNA.

EXAMPLE 10

Multicopy Effects of the cspA Upstream Region on Cold-shock Adaptation

It has been shown that the cspA gene is induced immediately after the temperature downshift from 37° C. to either 15 or 10° C. and that the rate of CspA production reaches a peak after 1 hr at 15° C. and 2 hr at 10° C. after the temperature shift (3) After this time point, CspA production sharply drops to a new basal level. The period of this transient production of CspA corresponds to the duration of growth arrest, known as the lag period, which is observed after cold shock (7). Thus, such a transient expression of CspA is considered to be required for cellular adaptation to lower temperatures.

Figure 9A:
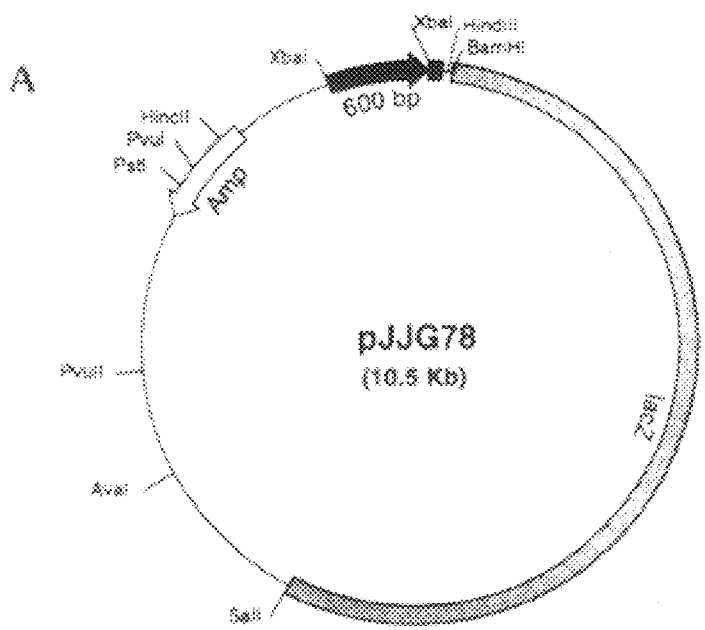
FIG. 9a shows a map of pJJG78 containing the transcriptional fusion of the 600-bp cspA upstream region and the lacZ gene.
Figure 9B:
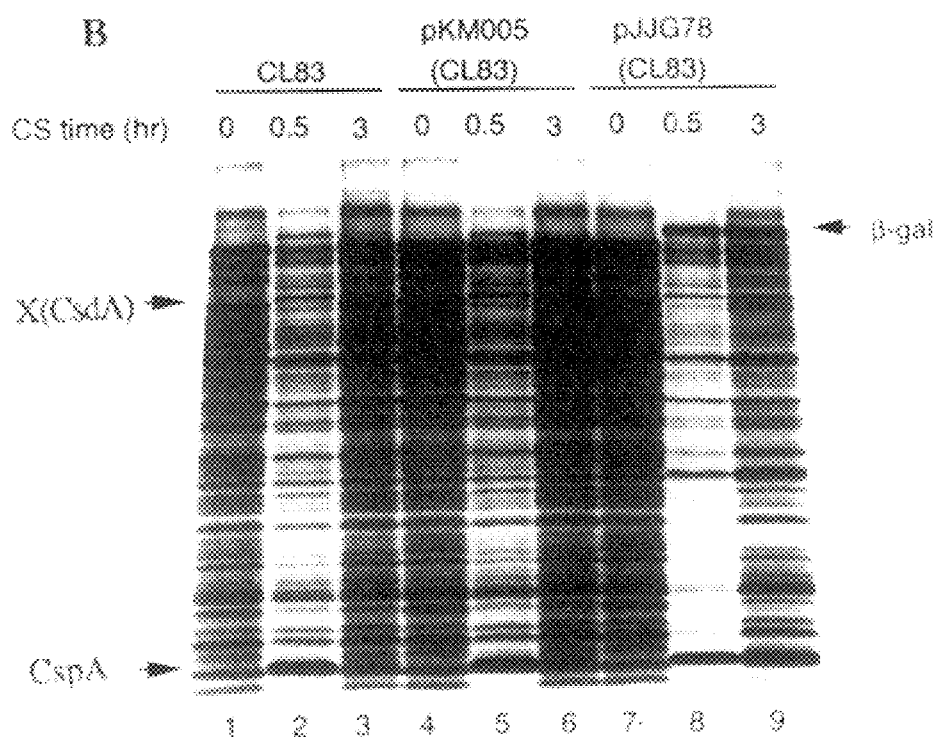
FIG. 9b shows the effects of the 600-bp upstream region of cspA.

In order to characterize this transient expression of cspA, we attempted to identify the region required for the regulation of the cspA expression during the adaptation period. For this purpose, pJJG78 was first constructed, in which the 600-bp cspA upstream region was transcriptionally fused to the lacZ gene (FIG. 9a). This 600-bp upstream region of cspA encompasses the region from −457 to +143 which is right before the Shine-Dalgarno sequence of cspA, as the cspA transcription initiation site is defined +1 (3). E. coli strain CL83 was transformed with pJJG78 and the production of β-galactosidase was examined by pulse-labeling cells with [35S]-methionine at 0, 0.5, and 3 hr after temperature downshift from 37 to 15° C. As controls, CL83 cells alone as well as CL83 cells transformed with vector pKM005 (4) were also used. As shown in FIG. 9b, for both CL83 and CL83/pKM005 the expression of cspA was highly induced at 0.5 hr after the temperature downshift (FIG. 9b, lanes 2 and 5, respectively). However, as shown previously (3), this high expression is transient and reduced to a new basal level at 3 hr (FIG. 9b, lanes 3 and 6, respectively). Note that no cspA expression was detected at 0 time point (FIG. 9b, lanes 1 and 4, respectively) and that β-galactosidase was not produced at any time point for both strains (FIG. 9b, lanes 1 to 6).

In contrast to CL83 and CL83/pKM005, β-galactosidase was clearly induced in the cells with pJJG78 upon the temperature downshift (FIG. 9b, lanes 7 to 9), indicating that the 600-bp upstream region of cspA is sufficient for the cold-shock induction. Surprisingly, the production of cspA was no longer transient but remained at a high level even 3 hr after cold shock in the cells harboring pJJG78 (FIG. 9b, compare lane 9 with lanes 3 and 6). Since pJJG78 does not contain the cspA coding sequence, the high production of cspA at 3 hr after temperature downshift is attributed to the chromosomal cspA gene. It appears that under the conditions used, the chromosomal cspA gene failed to be repressed, in other words it became derepressed. Interestingly, there is another band indicated by X in FIG. 9b, whose expression pattern was almost identical to that of cspA. It is a cold-shock protein and its production was also derepressed in the presence of pJJG78. This cold-shock protein X has been recently identified as CsdA which associates with ribosomes (10).

It should also be noted that the synthesis of most cellular proteins was blocked to a larger extent in the cells harboring pJJG78 at low temperature than that in the CL83 cells and CL83/pKM005 (FIG. 9b, compare lanes 8 and 9 to lanes 2, 3, 5, and 6). These results indicate that the cellular adaptation to the low temperature is impaired with a more severe cold-shock response when cells harbor a multicopy plasmid carrying a part of the cspA gene.

Figure 10:
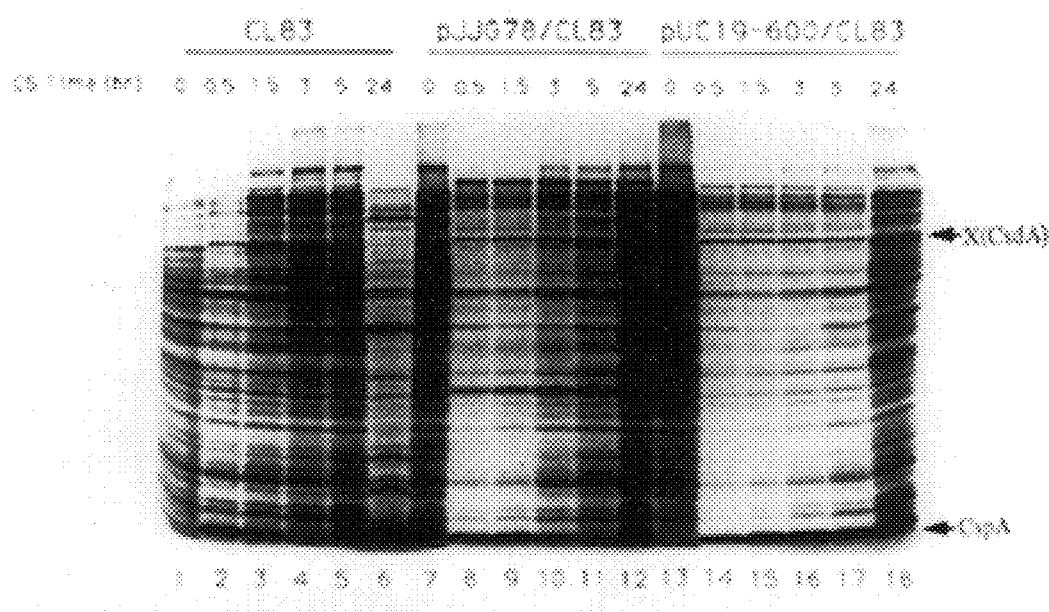
FIG. 10 shows the prolonged expression of CspA and inhibition of cold-shock adaptation by pJJG78 and pUC19-600.

Since the prolonged synthesis of CspA after cold-shock was caused by pJJG78, it was hypothesized that the 600-bp cspA upstream region cloned in pJJG78 may sequester a factor responsible for the inhibition of CspA production after cold shock, resulting in the prolonged expression or the derepression of cspA. In order to examine this hypothesis, the 600-bp upstream region of cspA was re-cloned into pUC19. The plasmid is called pUC19-600. Note that the copy number of pUC19 (300 copies/cell) is about 10 times higher than pJJG78 derived from pBR322 (30 copies/cell). A pulse-labeling experiment was carried out as described previously (6). As shown in FIG. 10, in the CL83 cells, CspA production increased up to 1.5 hr and was reduced to a basal level after 3 hr at 15° C. (FIG. 10, lanes 1 to 6). In CL83 cells with pJJG78, a certain level of cspA expression was still observed even after 24 hr at 15° C. (FIG. 10, lanes 7 to 12). Patterns of CspA production in CL83 cells with pUC19-600 are similar to those with pJJG78 (FIG. 10, lanes 13 to 18). However, the level of the cspA derepression was much higher with pUC19-600 than that with pJJG78, as nudged from the production of CspA at 3 and 5 hr. Thus, the higher the copy number of the cspA upstream region, the stronger the derepression of the CspA expression. Again, CsdA (indicated by X) showed the exactly same expression pattern as CspA throughout all the lanes shown in FIG. 10.

As shown in FIG. 9b, the cells with pJJG78 showed a certain inhibition of general protein synthesis at low temperature (compare lanes 8 to 11 with lanes 2 to 5, respectively in FIG. 10). Significantly, this inhibition in the cells harboring pUC19-600 was even more evident than that in the cells harboring pJJG78, in terms of both the protein synthesis rate and the inhibition time (compare lanes 14 to 17 with lanes 8 to 11, FIG. 10). The higher copy number of the 600-bp of cspA upstream region results in the stronger inhibition of the synthesis of other cellular proteins, indicating that cold-shock adaptation is inhibited.

EXAMPLE 11

Overproduction of the 5' Untranslated Region of the cspA mRNA

Figure 11:
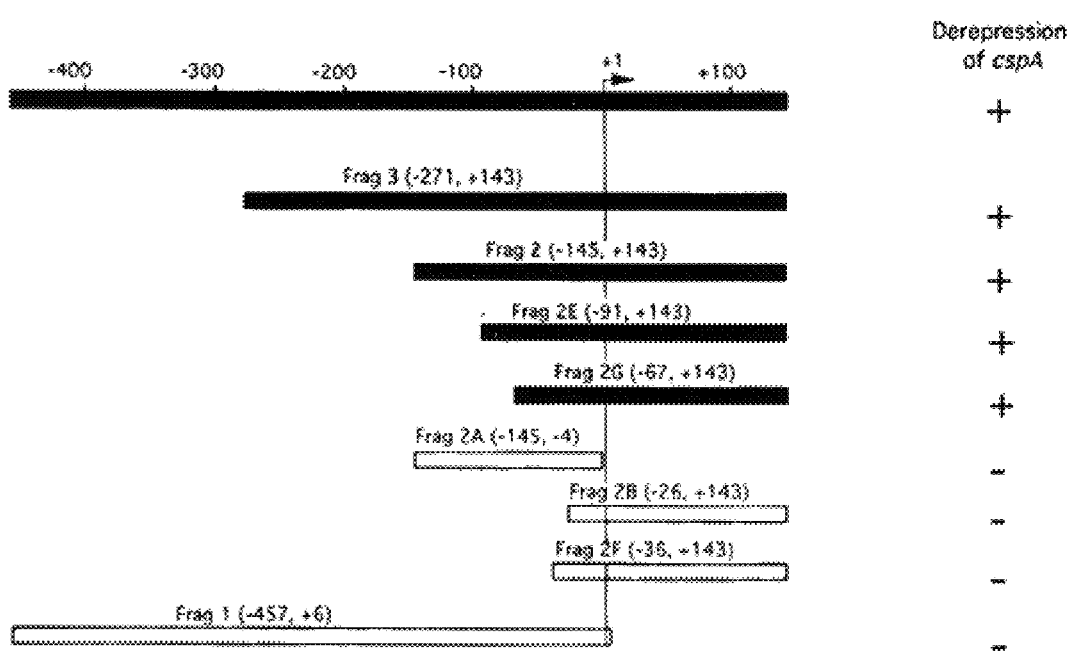
FIG. 11 shows deletion analysis of the cspA upstream region for the cspA derepression function and inhibition the cold-shock adaptation.

In order to determine the precise region within the 600-bp sequence required for the derepression of cspA and the inhibition of cold-shock adaptation at low temperature, a series of internal fragments as shown in FIG. 11 were generated by FOR and cloned into the SmaI site of pUC19. Their sequences were confirmed by DNA sequencing. The ability to derepress expression of cspA and to inhibit cold-shock adaptation at 15° C. for each construct was examined by pulse-labeling experiment. First, deletion mutations were made from the 5' end of the 600-bp fragment. As shown in FIG. 11, fragment 3 (186-base deletion), fragment 2 (312-base deletion), fragment 2E (366-base deletion) and fragment 2G (390-base deletion) all still retained the derepression function. Next, fragment 2 was further dissected into fragment 2A and 2B which overlap by 23 bp as shown in FIG. 11. Surprisingly, both 2A and 2B lost the functions. Fragment 2F which is longer by 33 bp at the 5' end than fragment 2B was also constructed, was still incapable of the functions. It was found here that the constructs which are capable of the derepression of cspA also result in inhibition of the cold-shock adaptation, and vice versa.

The fact that fragment 2 is functional for both the cspA derepression and the inhibition of cold-shock adaptation, while fragment 2A is not, indicates that the cspA promoter region alone is not sufficient for the functions of the 600-bp fragment. Furthermore, the fact that functional fragment 2G is longer at the 5' end by 31 bp than the non-functional fragment 2F suggests a possibility that the both functions require the full cspA promoter for the transcription of the 5' UTR of the cspA mRNA. Note that the cspA mRNA has a 159-base untranslated sequence at the 5' end (3). In order to confirm this possibility, the cspA transcripts produced from the cloned fragments (fragments 2, 2A, 2B, 2E, and 2F) were examined by primer extension. Using the total RNA fraction isolated from cells harboring various plasmids incubated for 1 hr at 15° C., primer extension was performed with two independent primers; primer 3550 which corresponds to the sequence from +124 to +143 in the 5' UTR and primer 3551 which corresponds to a part of the cspA coding sequence from +224 to +243. The former primer detects the cspA mRNA transcribed from both the plasmid and the chromosome, while the latter detects the mRNA only from the chromosomal cspA gene, since none of the plasmids contains the cspA coding region.

Figure 12:
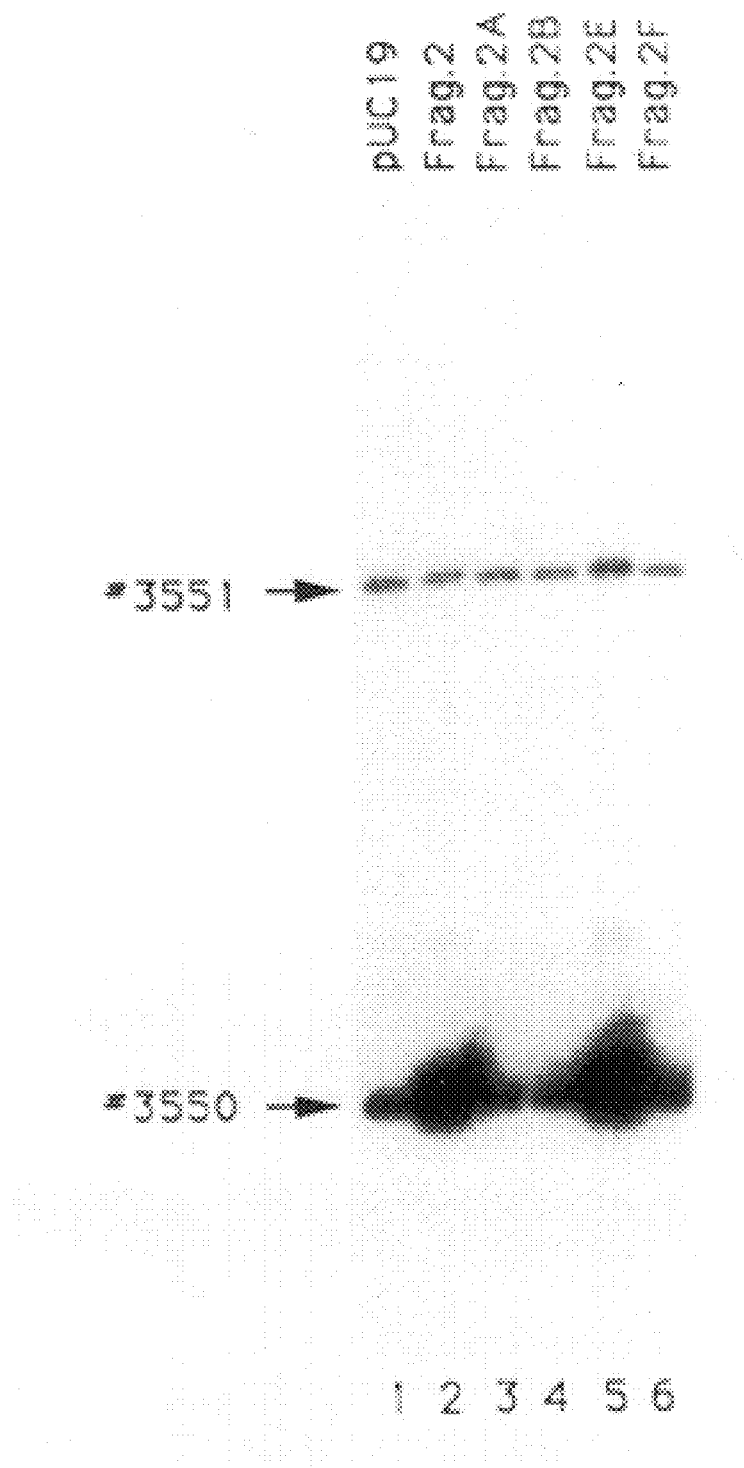
FIG. 12 shows the level of the transcripts from the chromosomal and plasmid cspA.

As shown in FIG. 12, the amounts of the transcript from the chromosomal cspA gene indicated by primer 3551 were basically the same among all constructs (FIG. 12, lanes 1 to 6). In contrast, the amount of the cspA transcripts encompassing the 5' UTR indicated by primer 3550 showed two different levels. For those unfunctional constructs (pUC19-2A, pUC19-2B, and pUC2F), the amounts of the transcripts detected by primer 3550 (lanes 3, 4, and 6 in FIG. 12, respectively) were almost identical to that with pUC19 (lane 1 in FIG. 12), indicating that the cspA regions cloned in these plasmids were not transcribed. On the other hand, for those functional constructs (pUC19-2 and pUC19-2E), much higher levels of the cspA transcripts detected by primer 3550 were observed (lanes 2 and 5 in FIG. 12, respectively) in comparison with the level with pUC19 (lane 1 in FIG. 12). These results demonstrate that the 5' UTR of the cspA mRNA was transcribed in fragment 2 and 2E, but not in fragments 2A, 2B and 2F. Therefore, the ability to prolong cspA expression and to inhibit the cold-shock adaptation at low temperature is clearly correlated with the transcription of the 5' UTR of the cspA mRNA.

Figure 13A:
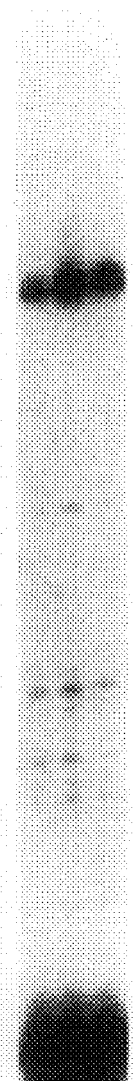
FIG. 13a shows the detection of transcripts from the cspA promoter in Fragment 1 using pJJG81/x,s.
Figure 13B:
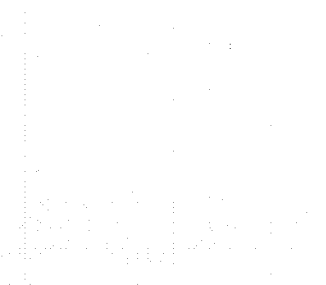
FIG. 13b is an SDS-PAGE analysis of protein synthesis of CL83 cells harboring pJJG81/x,s after cold-shock treatment.

In order to unambiguously demonstrate that the transcription of the 5' UTR of the cspA mRNA is required for both the cspA derepression and the inhibition of cold-shock adaptation, the entire promoter fragment (−457 to −1) plus 6-base (+1 to +6) region from cspA was cloned into pUC19. This fragment was designated fragment 1 (see FIG. 11) Thus, most of the 5' UTR of the cspA mRNA was deleted in fragment 1. By pulse-labeling experiment shown in FIG. 13b, fragment 1 was incapable of derepressing cspA, in spite of the fact that the transcripts from the cspA promoter were clearly detectable by primer extension (FIG. 13a). From these results, it is concluded that at least a portion of the cspA untranslated region from +1 to +143 has to be transcribed to exert the effect on the cspA expression and the cold-shock adaptation.

EXAMPLE 12

Cold-shock Genes Affected by the Overproduction of the 5' UTR of the cspA mRNA

Figure 14A:
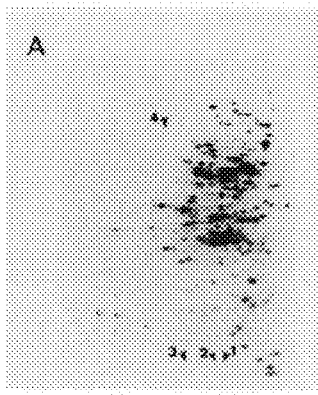
FIGS. 14a, c, and e show the protein expression patterns of CL83 cells harboring pJJG21/x,s at 37° C., 1 hour at 15° C., and 3 hours at 15° C., respectively.
Figure 14B:
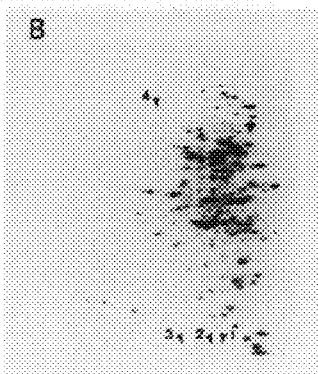
FIGS. 14b, d, and f show the protein expression patterns of CL83 cells harboring pJJG81/x,s at 37° C., 1 hour at 15° C., and 3 hours at ° C., respectively.
Figure 14C:
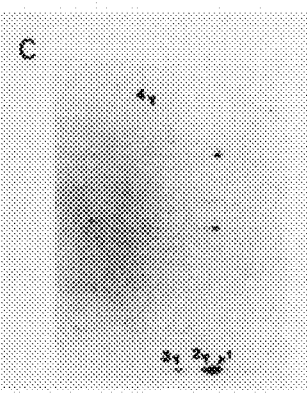
Figure 14D:
Figure 14E:
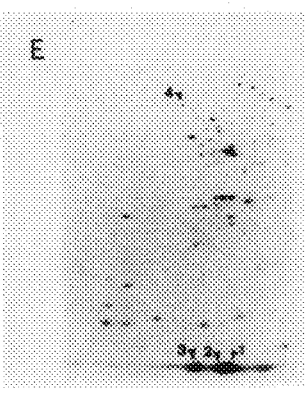
Figure 14F:
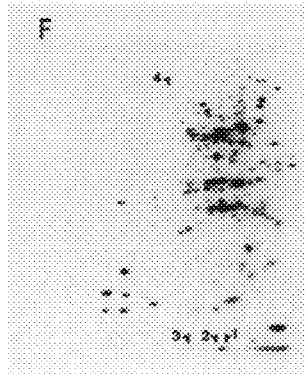

Next, the overproduction of the 5' UTR of the cspA mRNA was examined to determine if the cspA mRNA has any effects on the expression of other cold-shock genes. The protein expression pattern of the cold-shocked cells overproducing the cspA 5' UTR was analyzed by two-dimensional electrophoresis. The plasmid pJJG21/X,S contains the entire cspA promoter and most of the 5' UTR of the cspA mRNA (+1 to +143), while pJJG81/X,S contains the entire cspA promoter but only the first 6-base region of the cspA untranslated mRNA. The cells harboring these plasmids were pulse-labeled as described before (6). At 37° C., the rate of protein synthesis and the protein pattern were very similar for both strains (FIGS. 14, A and B); note that no cold-shock proteins were detected. When these cells were shifted to 15° C. for 1 hr (FIGS. 14, C and D), the synthesis of cold-shock proteins (1. CspA; 2. CspB'; 3. CspB; and CsdA) became very prominent. Note that CspB' was co-induced with CspB and had been speculated to be either a modified form of CspB or a yet unidentified cold-shock protein (2). The rate of cold-shock protein synthesis for both constructs was comparable as judges from the densities of the spots. Although the synthesis of most other cellular proteins was significantly reduced for both strains compared with that at 37° C., much stronger inhibitory effects were observed in the cells transformed with pJJG21/X,S. When cells were incubated at 15° C. for 3 hr, synthesis of most cellular proteins recovered to a normal level with concomitant reduction of all the cold-shock proteins in the cells harboring pJJG81/X,S (FIG. 14F). In contrast, for the cells harboring pJJG21/X,S, the production of all the cold-shock proteins (marked by 1 to 4) was still maintained at a very high level along with reduced production of other cellular proteins (FIG. 14E). These results clearly demonstrated that overproduction of the 5' UTR of the cspA mRNA results in the derepression of not only cspA but also other cold-shock genes, suggesting that genes for cold-shock proteins are regulated by a common mechanism. It is also further confirmed that the inhibition of cold-shock adaptation is due to the overproduction of 5' UTR of the cspA mRNA by blocking the synthesis of other cellular proteins. Based on the results described above, overproduction of the UTR of the cspA mRNA causes the concomitant inhibition of other cellular proteins. This implies that cell growth upon cold shock would be more severely inhibited with the cells overproducing the UTR of the cspA mRNA than that with the wild type cells. The growth of cells harboring pUC19-600 or pUC19-2G (see FIG. 11) was indeed severely inhibited. This was characterized by a longer lag period (data not shown).

EXAMPLE 13

Effects of the Overproduction of cspA

The overexpression of the 5' UTR of the cspA mRNA resulted in the prolonged overproduction of CspA (see FIG.

Figure 15:
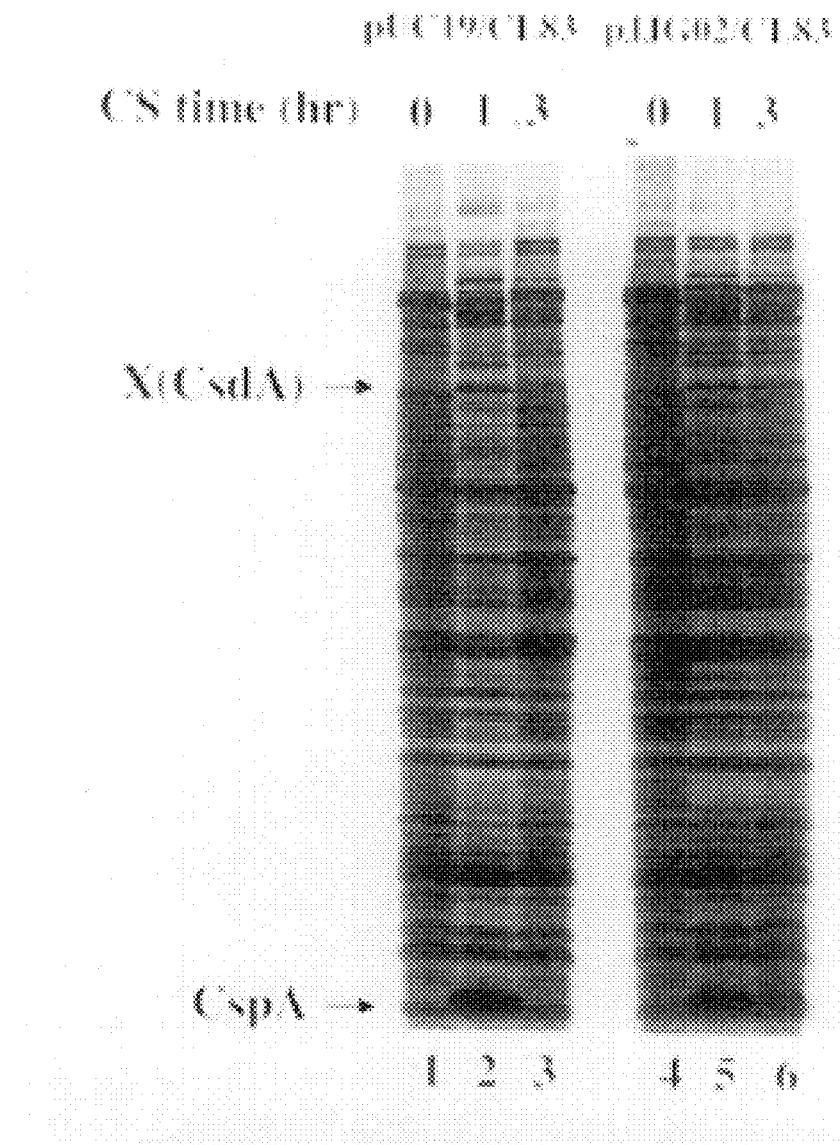
FIG. 15 shows the effects of co-overproduction of cspA together with the 5' untranslated region of the cspA mRNA on cold-shock response.

10). Therefore, the effects observed above may be due to the overproduction of the CspA protein rather than the 5' UTR of the cspA mRNA. This possibility was examined using CL83 cells harboring pJJG02 which contains the entire cspA gene. Pulse-labeling experiments were carried out as described above. As shown in FIG. 15, with strain CL83 carrying pUC19, the expression of cspA and csdA (the gene for protein X) were induced at 1 hr after the temperature shift to 15° C. (lanes 1 and 2), and returned to a basal level at 3 hr after the temperature shift (lane 3). On the other hand, when the cells were transformed with pJJG02, the expression of cspA was not only induced at 15° C., but also significantly higher than that of cells with pUC19 as judged by two-dimensional gel electrophoresis (not shown). It should be noted that high CspA production is still observed even at 3 hr 15° C. (lane 6). Although this overproduction of CspA at 3 hr after cold-shock was very similar to the case with the overproduction of the 5' UTR of cspA as described earlier (FIG. 10), it is important to note that no prolonged lag period of cell growth and no prolonged production of other cold-shock proteins such as CspB and CsdA were observed at the same time point. These results indicate that the co-production of CspA with the 5' UTR of the cspA mRNA suppresses the effects of the overproduction of only the 5' UTR, and that the high levels of CspA production even at 3 hr after cold-shock are not the cause of this effect.

DISCUSSION OF RESULTS

Cold-shock response in terms of protein synthesis is characterized by the transient expression of cold-shock genes. Upon temperature downshift, a number of cold-shock genes such as cspA, cspB and csdA are dramatically induced (3, 9, 10). However, the expression is soon reduced to a new basal level. Such transient expression of cold-shock genes is considered to be essential for cellular adaptation to low temperature, since the lag period of cell growth upon cold shock corresponds to the period of the transient expression of cold-shock genes (7, 8). In this invention it is demonstrated that when the 5' UTR of the cspA mRNA was overproduced upon cold shock, cells failed to properly respond to the stress as summarized: (a) Expression of cold-shock genes is no longer transient. (b) In contrast to cold-shock proteins, the synthesis of other cellular proteins is severely impaired for a long time; there is a reciprocal relationship between the production of cold-shock proteins and the production of other cellular proteins. (c) The temporary cessation of cell growth normally observed upon cold shock is also prolonged.

On the basis of these results, it is possible to postulate that cold-shock gene products are essential for cellular adaptation to low temperature likely required for more efficient translation, transcription and/or DNA replication. These adaptive processes cause temporary inhibition of the synthesis of other non-cold-shock proteins, which results in temporary cessation or a lag period of cell growth. The induced production of cold-shock proteins has to be reduced or repressed to a new basal level, which then permits the synthesis of other cellular proteins, and thereby normal cell growth is resumed. At present, the mechanism of the reciprocal relationship between the synthesis of cold-shock proteins and other cellular proteins is unknown. However, the present results clearly demonstrate that the unusually long 5' UTR of the cspA mRNA (159 bases) (3) plays an important role in the repression of the highly induced expression of not only its own gene, cspA, but also other cold-shock genes such as cspB and csdA.

Figures 16A, 16B:
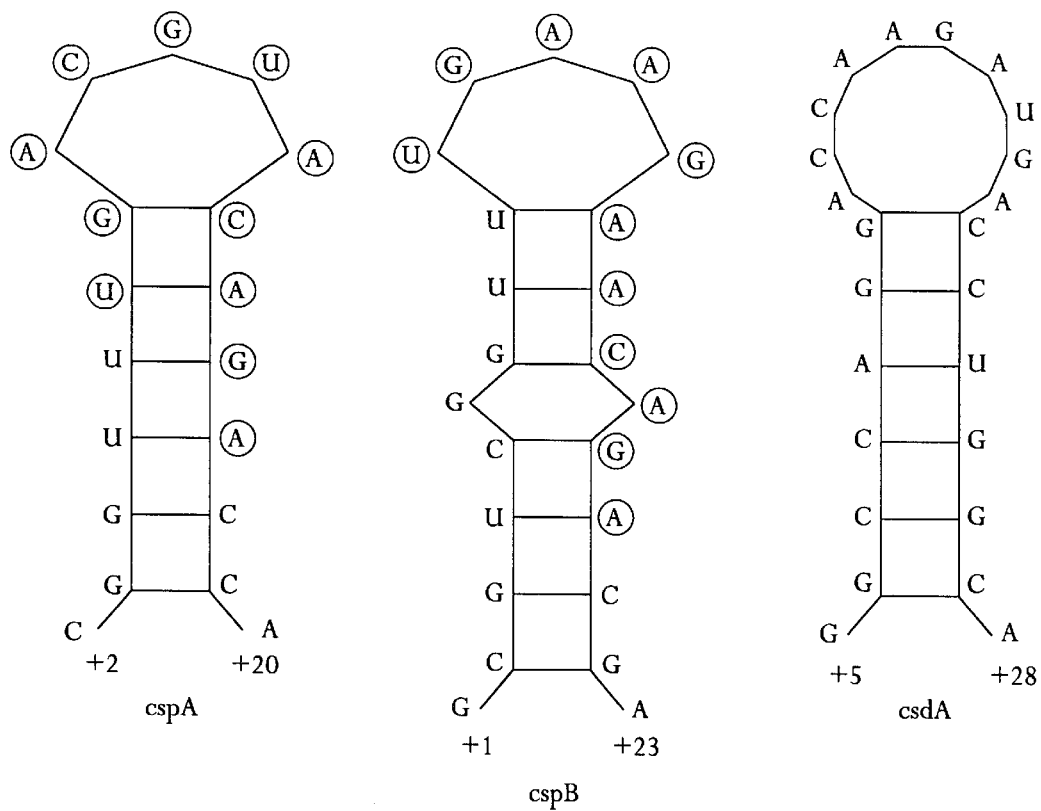
FIG. 16a shows sequence similarities in the 5' untranslated regions of mRNA for cspA (SEQ ID NO:11), cspB (SEQ ID NO:10), and csdA (SEQ ID NO:12). The consensus sequence is also shown (SEQ ID NO:13).
FIG. 16b shows a schematic representation of cspA, cspB, and csdA.

It is interesting to note that cspA, cspB (2) and csdA (10) all produce mRNAs with unusually long 5' UTRs (159 (SEQ ID NO:48), 161 (SEQ ID NO:55), and 226 (SEQ ID NO:56) bases, respectively). Within these UTRs, a highly homologous sequence comprised of 11 bases, and designated the "cold box" is found in each mRNA (FIG. 16A). There are only 2 and 1 mismatches in the cold boxes between cspA and cspB, and between cspA and csdA respectively. The consensus sequence of the cold box is UGACGUACAGA as shown in FIG. 16A. It is tempting to speculate that the cold box is the repressor binding site. It is important to note that as the cspA production decreases during cold-shock adaptation, the amount of the cspA mRNA almost parallelly decreases (17). This result indicates that the repression of cspA during cold-shock adaptation is proportional to the amount of the cspA mRNA, and that it is not regulated at the level of translation. We propose that a putative cold-shock inducible repressor binds to the cold-box sequence common to the cold-shock mRNAs which in turn inhibits the transcription of these genes (hypothesis I) or destabilizes their mRNAs (hypothesis II). The result shown in FIG. 15 indeed supports this proposal, where the region responsible for the cspA derepression exists within the first 25-base sequence of the cspA mRNA. Furthermore, the csdA 5' UTR was also able to derepress the cspA expression at low temperature when it was expressed under the cspA promoter (not shown).

In accordance with the invention, it is proposed that the repressor binding to the cold-box interferes with further transcription of the genes. How the repressor binding to mRNA inhibits the function of RNA polymerase in cis to block further RNA elongation is not known at present. The putative repressor is considered to be cold-shock inducible so that when its cellular level becomes higher than a certain threshold it binds to the cold boxes on the cold-shock inducible mRNAs. Therefore the overproduction of a part of mRNA containing a cold box sequesters the repressor, resulting in derepression of cold-shock gene expression. In hypothesis II, cold-inducible factor or repressor binds to the cold-box sequence, which destabilizes the cold-shock mRNAs to reduce their cellular contents. This in turn results in the reduction of the production of cold-shock proteins.

Since the co-overproduction of CspA together with the 5' UTR resumed the normal cold-shock response, CspA itself is likely to be either directly or indirectly involved in the function of the repressor. CspA, which has been proposed to function as an RNA chaperone (9), may bind to the cold box or cold-box associated structures. If so, it is an interesting question how CspA binding on an mRNA causes the attenuation of transcription, or destabilization of the mRNA.

MATERIALS AND METHODS

E. coli strain and culture medium. E.coli CL83 [recA ara (lac-proAB) rpsL(=strA) f80 lacZ M15] (12) was used for all experiments and was grown in M9-Casamino acids medium as described previously (13). For pulse-labeling experiments, an amino acid mixture which lacks methionine was used. The final concentration of each amino acid was 50 µg/ml.

Plasmid Construction pJJG02 was constructed from pJJG01 (3) as follows: A 998-bp fragment which contains the entire cspA gene was obtained from pJJG01 by HindIII and XmnI digestion. This fragment was then treated with the Klenow fragment of DNA polymerase (Life Technologies), and inserted into the SmaI site of pUC9.

pJJG21 was constructed from pJJG02 by creating an XbaI site immediately upstream of the Shine-Dalgarno sequence of cspA as follows: +138AATT<u>T</u>(A)<u>C</u>(T)TA<u>G</u>(A)AG GTAA+153 (SEQ ID NO:25) (the original nucleotides in the parenthesis were substituted by the underlined nucleotides; ref. 1). pJJG81 was constructed from pJJG02 by creating an XbaI site immediately downstream of the transcription initiation site of cspA as follows: +1ACGGTT<u>CT</u> <u>A</u>GACGTA+15 (SEQ ID NO:38) (nucleotides underlined represent the inserted bases)

pJJG78 is a transcriptional fusion of the 0.6-kb cspA upstream region and lacZ as follows: the 1-kb EcoRI/BamHI fragment containing cspA from pJJG21 was filled in with Klenow enzyme and ligated into the SmaI site of pUC19. Then, the 0.6-kb XbaI fragment containing the cspA regulatory region (from −457 to +143) was excised and ligated into the XbaI site in pKM005 (4) in the correct orientation.

pUC19-600 was constructed by insertion of the 0.6-kb EcoRI/XbaI containing fragment 1 (FIG. 11) was constructed by removing the 0.74-kb XbaI/SalI fragment from pJJG81. Both ends were treated with Klenow fragment, followed by self-ligation. All the other constructs shown in FIG. 3 were made by PCR (Boehringer Mannheim protocol). PCR amplified fragments were inserted into the SmaI site of pUC19. All PCR products were confirmed by DNA sequencing (15).

p2JTEK was constructed as follows: PCR product by primer 3549 5'CGGCATTAAGTAAGCAGTTG 3' (SEQ ID NO:39) and primer 4428 5'CTGGATCCTTTAATGGTCT-GTACGTCAAACCGT 3' (SEQ ID NO:40) was cloned into the SmaI site of pUC19. This PCR product contains cspA from −146 to +25 as the cspA transcription start site is defined as +1. Then the transcriptional terminator of cspA was amplified by PCR using primer 6290 5'CGGAAT-TCAGCCTGTAATCTCT 3' (SEQ ID NO:41) and 4860 5' CTGTCGACTTACTTACGGCGTTGC 3' (SEQ ID NO:42). The PCR product was then digested with EcoRI then cloned into the plasmid described above which was digested with EcoRI and SspI. The 52-bp KpnI and EcoRI fragment from pBluescript II SK was then cloned into EcoRI and KpnI site. All PCR products were confirmed by DNA sequencing (15).

p6mTEK was constructed in the same way as p2JTEK except that the first PCR was carried out with different primers: primer 3552 5' GACAGGATTAAAAATCGAG 3' (SEQ ID NO:43) and 6196 5' AACCGTTGATGTGCA (SEQ ID NO:44). This PCR product encompasses cspA from −278 to +6 as the cspA transcription start site is defined as +1. All PCR products were confirmed by DNA sequencing (15).

The pulse-labeling experiments were carried out as described previously (6). Proteins were analyzed either by polyacrylamide SDS-gel electrophoresis (5) or by two-dimensional electrophoresis as described previously (7).

Primers Used for Primer Extension Experiments

Primer 3550 [5'-TAATTAAGTGTGCCTTTCGG-3'] (SEQ ID NO:45) corresponds to the sequence from +143 to +124 nt with the cspA transcription initiation site defined is +1 (Goldstein et al. 1990). Primer 3551 [5'-TTTAGAGCCATCGTCAGGAG-3'] (SEQ ID NO:46) is from +243 to +224 nt. The reverse primer [5'-TTCACACAGGAAACAGCTAT-3'] (SEQ ID NO:47) corresponds to the sequence of pUC9 from 468 to 487 nt (19). The primer was labeled at the 5'-end by [g-32P]ATP with T4 kinase (Life Technologies) as described previously (6). RNA was extracted according to the method described previously (6).

FIGURE LEGENDS

FIGS. 1–8 are described herein above.

FIG. 9. (A) Map of pJJG78 containing the transcriptional fusion of the 600-bp cspA upstream region and the lacZ gene. The construction of pJJG78 was described in Materials and Methods. The 600-bp cspA upstream region corresponds to the sequence from −457 to +143 base of (B) The effects of the 600-bp upstream region of cspA.

Pulse-labeling experiments were carried out as described in Materials and Methods. Cell cultures were shifted from 37 to 15° C. at a mid-log phase (80 Klett unit). The time point of pulse-labeling is shown above each lane. The same culture volume (0.25 ml) was used for each time point and the pulse-labeling times at 37 and 15° C. were 5 and 15 min, respectively. The positions of CspA, β-galactosidase and CsdA (protein X) are indicated by arrows. Lanes 1 to 3, host cell CL83; lanes 4 to 6, CL83 cells harboring pKM005; and lanes 7 to 9, CL83 cells harboring pJJG78. The band seen just below CspA has been identified to be the major outer membrane lipoprotein (lanes 1, 3, 4, 6 and 7).

FIG. 10. Pulse-labeling experiments with strain CL83 and CL83 harboring pJJG78 or pUC19-600 were carried out as described in Materials and Methods. Constructs tested and the time points of pulse-labeling are indicated on the top of the lanes. CspA and protein X (CsdA) are indicated by arrows. Lanes 1 to 6, CL83 cells; lanes 7 to 12, CL83 cells harboring pJJG78; and lanes 13 to 18, CL83 cells harboring pUC19-600.

FIG. 11. The full length 600-bp cspA upstream region is shown on the top. The name, the 5'- and 3'-end positions of each fragment are shown above each bar. The ability to derepress the cspA expression during the cold-shock adaptation process is indicated + or − as judged by the CspA production at 3 hr after temperature downshift. Solid bars indicate clones which are capable of derepressing the chromosomal cspA gene; and open bars, incapable of derepressing cspA.

FIG. 12. The name of each construct is shown on the top of each lane. Two different primers (primer 3550 and 3551) were separately used for primer extension using the same amount of total cellular RNA. In each lane, equal volume of the two reactions were mixed and loaded on 7 M urea-6% polyacrylamide gel. The expected extension products are indicated by the primer number.

FIG. 13. (A) Detection of transcripts from the cspA promoter in fragment 1 (FIG. 11) using pJJG81/X,S. The primer extension experiment was done as described in Materials and Methods. The reverse primer from pUC19 was used to detect the transcripts from the cspA promoter in fragment 1. The time points after cold shock are indicated on the top of lanes. (B) SDS-PAGE analysis of protein synthesis of CL83 cells harboring pJJG81/X,S after cold-shock treatment (37 to 15° C.). Pulse-labeling experiments were carried out as described in Materials and Methods. The time points of pulse-labeling are shown on the tops of lanes. CspA and protein X (CsdA) are indicated by arrows.

FIG. 14. Pulse-labeling experiments and the two-dimensional electrophoresis were carried out as described in Materials and Methods. A, C, and E show the protein expression patterns of CL83 cells harboring pJJG21/X,S at 37° C., 1 hr at 15° C., and 3 hr at 15° C., respectively. B, D, and F show the protein expression patterns of CL83 cells harboring pJJG81/X,S at 37° C., 1 hr at 15° C. and 3 hr at 15° C., respectively. The cold-shock proteins are indicated by arrows. Arrow 1, CspA; arrow 2, CspB'; arrow 3, CspB, and arrow 4, CsdA.

FIG. 15. CL83 cells harboring pUC19 and pJJG02 were pulse-labeled at 37° C. (lanes 1 and 4, respectively), 15° C. 1 hr (lanes 2 and 5, respectively) and 3 hr (lanes 3 and 6, respectively) analyzed by SDS-polyacrylamide gel electrophoresis as described in Materials and Methods. CspA and protein X (CsdA) are indicated by arrows.

FIG. 16. CL83 cells harboring pUC19 (lane 1), p6mTEK (lane 2) and p2JTEK (lane 3) were pause-labeled at 15° C. 3 hr. Labeled total cell extracts were then analyzed by SDS-polyacrylamide gel electrophoresis as described in Materials and Methods. CspA and protein X (CsdA) are indicated by arrows.

FIG. 17. The highly homologous sequences of 11 bases are boxed and designated "cold box". The consensus cold box sequence is shown at the bottom. Identical bases are connected by vertical lines.

All references referred to herein are incorporated by reference.

In light of the foregoing description, many modifications, alterations, and substitutions are possible in the practice of the invention without departing from the spirit or scope thereof. It is intended that such modifications, alterations, and substitutions be included in the scope of the claims.

REFERENCES

1. Doniger, J., D. Landsman, M. A. Gonda, and G. Wistow. 1992. The product of unr, the highly conserved gene upstream of N-ras, contains multiple repeats similar to the cold-shock domain (CSD), a putative DNA-binding motif. The New Biologist 4:389–396.

2. Etchegaray, J. P., P. G. Jones, and M. Inouye. 1996. Differential thermoregulation of two highly homologous cold-shock genes, cspA and cspB, of *Escherichia coli*. Genes to Cells. in press.

3. Goldstein, J., N. S. Pollitt, and M. Inouye, 1990. Major cold-shock protein of *Escherichia coli*. Proc. Natl. Acad. Sci. USA 87:283–287.

4. Inouye, M., ed. 1983. Experimental manipulation of gene expression. pp. 28–30. Academic Press, Inc. Orlando, Fla.

5. Inouye, S., X. Soheron, T. Franceschini, K. Nakamura, K. Hakura, and M. Inouye. 1982. Role of positive charge on the amino-terminal region of the signal peptide in protein secretion across the membrane. Proc. Natl. Acad. Sci. USA 79:3438–3441.

6. Jiang, W., P. G. Jones, and M. Inouye. 1993. Chloramphenicol induces the transcription of the major cold-shock gene of *Esohericlila coli*, cspA. J. Bacteriol. 175:5824–5828.

7. Jones, P. G., R. A. VanBogelen, and F. C. Neidhardt. 1987. Induction of proteins in response to low temperature in *Escherichia coli*. J. Bacteriol. 169:2092–2095.

8. Jones, P. G., M. Cashel, G. Glaser, and F. C. Neidhardt. 1992. Function of a relaxed-like state following temperature downshifts in *Escherichia coli*. J. Bacteriol. 174:3903–3904.

9. Jones, P. G. and M. Inouye. 1994. The cold-shock response—a hot topic. Mol. Microbiol. 11:811–818.

10. Jones, P. G., M. Mitta, Y. Kim, W. Jiang, and M. Inouye. 1995. Cold shock induces a new major ribosomal-associated protein which unwinds double-stranded RNA in *Escherichia coli*. Proc. Natl. Acad. Sci. USA 93:76–80.

11. Lee, S. J., A. Xie, W, Jiang, J. -P. Etchegaray, P. G. Jones, and M. Inouye. 1994. Family of the major sold-shock protein, cspA(CS7.4) of *Escherichia coli*, whose members show a high sequence similarity with the Eukaryotic Y-box binding proteins. Mol. Microbiol. 11:833–839.

12. Lerner, C. G. and M. Inouye. 1990. Low copy number plasmids for regulated low-level expression of cloned genes in *Escherichia coli* with blue/white insert screening capability Nucl. Acids Res. 18:4631.

13. Miller, J. H., ed 1972. Experiments in molecular genetics. pp 352–355. Cold Spring Harbor Laboratory, Cold Spring Harbor, N.Y.

14. Newkirk, K., W. Feng, W. Jiang, R. Tejero, S. D. Emerson, M. Inouye, and G. Montelione. 1994. Solution NMR structure of the major cold-shock protein (CspA) from *Esoherichia coli*: identification of a binding epitope for single-stranded DNA. Proc. Natl. Acad. Sci. 91:5114–5118.

15. Sanger, F., S. Nicklen, and A. R. Coulsen. 1977. DNA sequencing with chain-termination inhibitors. Proc. Natl. Acad. Sci. USA 74:5463–5467.

16. Schindelin, H., W. Jiang, M. Inouye, and U. Heinemann. 1994. Crystal structure of the major cold-shock protein of *Escherichia coli*. Proc. Natl. Acad. Sci. USA 91:5119–5123.

17. Tanabe, H., J. Goldstein, M. Yang, and M. Inouye. 1992. Identification of the promoter region of the *Esoherichia coli* major cold-shock gene, cspA. J. Bacteriol. 174:3867–3873.

18. Toone, W. M., K. E. Rudd, and J. D. Friesen. 1991. dead, a new *Esoherichia coli* gene encoding a presumed ATP-dependent RNA helicase, can suppress a mutation in rpsB, the gene encoding ribosomal protein S2. J. Bacteriol. 173:3291–3302.

19. Vieira, J. and J. Messing. 1982. The pUC plasmids, an M13mp7-derived system for insertion mutagenesis and sequencing with synthetic universal primers. Gene 19:259–268.

20. Wolffe, A. P., S. Tafuri, M. Ranjan, and M. Familari. 1992. The Y-box factors: a family of nucleic acid binding protein conserved from *Escherichia coli* to man. New Biol. 4:290–298.

21. Wolffe, A. P. 1994. Structural and functional properties of the evolutionarily ancient Ybox family of nucleic acid binding proteins. BioEssays. 16:245–251.

22. Yamanaka, K., T. Mitani, T. Ogura, H. Niki, and S. Hiraga. 1994. Cloning; sequencing, and characterization of multicopy suppressors of a mukB mutation in *Escherichia coli*. Mol. Microbiol. 13:301–312

What is claimed is:

1. A method for inhibiting protein translation in a bacterium comprising overexpressing in the bacterium an mRNA selected from the group consisting of cspA mRNA, cspB mRNA and csdA mRNA, which comprises an initiation codon and a downstream box nucleotide sequence 3' to the initiation codon which sequence is complementary to the antidownstream box of the 16S rRNA of the bacterium, and allowing the mRNA to anneal to the anti-downstream box, thereby binding the 16S rRNA and inhibiting translation of other bacterial mRNAs.

2. The method of claim 2 wherein the overexpressing is by transforming the bacterium with a cloning vector containing a DNA sequence which transcribes the mRNA.

3. The method of claim 2 wherein the DNA contains a promoter sequence 5' to the mRNA transcribing sequence.

4. The method of claim 1 wherein the initiation codon is selected from the group consisting of AUG, GUG, and UUG.

5. The method of claim 1 wherein the downstream box sequence overlaps the initiation codon.

6. The method of claim 1 wherein the downstream box is positioned 3' to the initiation codon at a distance between 0 and 30 nucleotides from the 3' end of the initiation codon.

7. The method of claim 6 wherein the distance is between 9 and 15 nucleotides.

8. The method of claim 1 wherein the downstream box is between 6 and 20 nucleotides in length.

9. The method of claim 8 wherein the downstream box is between 8 and 14 nucleotides in length.

10. The method of claim 1 wherein the bacterium is *E. coli*.

11. The method of claim 1 wherein the mRNA comprises an untranslated region 5' to the initiation codon.

12. The method of claim 1 wherein the untranslated region comprises a Shine-Dalgarno region.

13. The method of claim 1 wherein the mRNA comprises, 3' to the downstream box, a sequence which encodes a polypeptide.

14. The method of claim 1 wherein the inhibition of translation occurs at physiologic growth temperature of the bacterium.

15. The method of claim 1 wherein the inhibition of translation occurs at a temperature below the physiologic growth temperature of the bacterium.

16. A oligonucleotide RNA construct comprising an initiation codon and a downstream box nucleotide sequence 3' to the initiation codon which sequence is at least in part complementary to the anti-downstream box of the 16S rRNA of a bacterium, wherein the RNA is an isolated RNA construct or is transcribed from an isolated DNA construct and wherein the downstream box which is complementary to at least a part of the 16S rRNA of a bacterium is selected from the group consisting of SEQ ID NO:18, SEQ ID NO:19, SEQ ID NO:20, SEQ ID NO:21, and SEQ ID NO:22.

17. The RNA construct of claim 16 wherein the initiation codon is selected from the group consisting of AUG, GUG, and UUG.

18. The RNA construct of claim 16 wherein the downstream box sequence overlaps the initiation codon.

19. The RNA construct of claim 16 wherein the downstream box is positioned 3' to the initiation codon at a distance between 0 and 30 nucleotides from the 3' end of the initiation codon.

20. The RNA construct of claim 19 wherein the distance is between 9 and 15 nucleotides.

21. The RNA construct of claim 20 wherein the distance is 12 nucleotides.

22. The isolated RNA construct of claim 16 wherein the anti-downstream box has the sequence of SEQ ID NO:17.

23. An isolated oligonucleotide DNA construct which transcribes an mRNA comprising an initiation codon and a downstream box nucleotide sequence 3' to the initiation codon which sequence is complementary to at least a part of the anti-downstream box of the 16S rRNA of a bacterium, and wherein the mRNA transcribed by the DNA comprises mRNA selected from the group consisting of SEQ ID NO:18, SEQ ID NO:19, SEQ ID NO:20, SEQ ID NO:21, and SEQ ID NO:22.

24. The isolated DNA construct of claim 23 which further comprises a promoter element 5' to the initiation codon.

25. The isolated DNA construct of claim 23 wherein the initiation codon is selected from the group consisting of AUG, GUG, and UUG.

26. The isolated DNA construct of claim 23 wherein the downstream box sequence overlaps the initiation codon.

27. The isolted DNA construct of claim 23 wherein the downstream box is positioned 3' to the initiation codon at a distance between 0 and 30 nucleotides from the 3' end of the initiation codon.

28. The isolated DNA construct of claim 27 wherein the distance is between 9 and 15 nucleotides.

29. The isolated DNA construct of claim 28 wherein the distance is 12 nucleotides.

30. The isolated DNA consruct of claim 23 wherein the downstream box is between 6 and 20 nucleotides in length.

31. The isolated DNA construct of claim 23 which contains a Shine-Dalgarno region 5' to the initiation codon.

32. The replication cloning vector which contains a DNA promoter sequence operably linked to a DNA sequence which codes for an mRNA which comprises an initiation codon and a downstream box nucleotide sequence 3' to the initiation codon which sequence is complementary to at least a part of the anti-downstream box of the 16S rRNA of a bacterium and which mRNA comprises a sequence selected from the group consisting of SEQ ID NO:18, SEQ ID NO:19, SEQ ID NO:20, SEQ ID NO:21, and SEQ ID NO:22.

33. A bacterium which has been transformed with the cloning vector of claim 32.

34. A process to modify the cold shock response of a bacterium comprising transforming the bacterium to overproduce part or all of the 5' untranslated region of mRNA selected from the group of cold shock proteins consisting of cspA, cspB, and csdA and subjecting the bacterium to environmental or growth conditions that elicit the cold shock response of the bacterium.

35. The process of claim 34 wherein the modification is a prolongation of the lag period of cell growth and persistence of the synthesis of cold shock proteins following exposure of the bacterium to environmental or growth conditions that elicit the cold shock response.

36. The process of claim 34 wherein the 5' untranslated region comprises the entire promoter sequence of the cold shock protein.

37. The process of claim 34 which further comprises transforming the bacterium to overproduce CspA.

38. The process of claim 37 wherein the overproduction of CspA counteracts the effects of the overproduction of the 5' untranslated region.

39. The process of claim 34 wherein the modification is an overproduction of the desired protein encoded by a gene which is located downstream of the 5' untranslated region.

40. The method for protein production in a bacterium under environmental or growth conditions that elicit the cold shock response of the bacterium, wherein said method comprises transforming the bacterium with a gene encoding a downstream box, wherein the downstream box is complementary to at least a part of the 16S rRNA of a bacterium is selected from the group consisting of SEQ ID NO:18, SEQ ID NO:19, SEQ ID NO:20, SEQ ID NO:21, and SEQ ID NO:22.

41. An isolated DNA construct that directs the prolonged expression of a heterologous gene in a bacterium under environmental or growth conditions that elicit the cold shock response of the bacterium wherein the DNA construct transcribes mRNA selected from the group consisting of SEQ ID NO:18, SEQ ID NO:19, SEQ ID NO:21, and SEQ ID NO:22.

42. The isolated DNA construct of claim 41 wherein the bacterium is subjected to cold shock by exposure to a temperature of about 15° C. or lower.

43. The isolated DNA construct of claim 41 that blocks the synthesis of endogenous bacterial proteins at reduced temperature.

44. The isolated DNA construct of claim 41 that promotes the prolonged expression of a heterologous gene and blocks the synthesis of endogenous bacterial proteins and the growth of a bacterium under environmental or growth conditions that elicit the cold shock response of the bacterium, and wherein the construct comprises the nucleotides shown in a sequence selected from the group consisting of SEQ ID NO:55 and SEQ ID NO:58.

45. The isolated DNA construct of claim 41 that comprises a promoter region and at least part of the 5' untranslated region (UTR) of a cold shock inducible gene.

46. The isolated DNA construct of claim 46 in which the 5' UTR is that of CspA.

47. The isolated DNA construct of claim 46 in which the 5' UTR is that of csdA.

48. The isolated DNA consruct of claim 46 in which the promoter is the csdA promoter.

49. The isolated DNA construct of claim 41 comprising a heterologous promoter and a 5' UTR from a cold shock inducible gene.

50. A replication cloning vector comprising the DNA construct of claims 41–45 or 47–49.

51. A transformed bacterium containing the replication cloning vector of claim 49.

52. A method for overexpressing a heterologous gene in a transformed bacterium by subjecting the bacterium under environmental or growth conditions that elicit the cold shock response of the bacterium, said transformed bacterium comprising a replication cloning vector comprising the DNA construct of claim 41–45 or 47–49 fused upstream of said heterologous gene.

* * * * *

SEQUENCE LISTING

```
<160> NUMBER OF SEQ ID NOS: 58

<210> SEQ ID NO 1
<211> LENGTH: 1205
<212> TYPE: DNA
<213> ORGANISM: E. coli
<220> FEATURE:
<221> NAME/KEY: CDS
<222> LOCATION: (617)..(826)
```

-continued

```
<400> SEQUENCE: 1
aagcttcgat gcaattcacg atcccgcagt gtgatttgag gagttttcaa tggaatataa      60
agatccaatg catgagctgt tgagcagcct ggaacagatt gtttttaaag atgaaacgca     120
gaaaattacc ctgacgcaca gaacaacgtc ctgtaccgaa attgagcagt tacgaaaagg     180
gacaggatta aaaatggatg atttcgcccg ggttttgggc gtatcagtcg ccatggtaaa     240
ggaatgggaa tccagacgcg tgaagccttc aagtgccgaa ctaaaattga tgcgtttgat     300
tcaagccaac ccggcattaa gtaagcagtt gatggaatag actttatcca cttatgctgt     360
ttacggtcct gatgacagac cgttttccaa ccgattaatc ataaatatga aaataattg      420 ttgcatcacc cgccaatgcg tggcttaatg cacatcaacg gtttgacgta cagaccatta    480
aagcagtgta gtaaggcaag tcccttcaag agttatcgtt gatacccctc gtagtgcaca    540
ttcctttaac gcttcaaaat ctgtaaagca cgccatatcg ccgaaaggca cacttaatta    600
ttaaaggtaa tacact atg tcc ggt aaa atg act ggt atc gta aaa tgg ttc    652
               Met Ser Gly Lys Met Thr Gly Ile Val Lys Trp Phe
                 1               5                  10 aac gct gac aaa ggc ttc ggc ttc atc act cct gac gat ggc tct aaa        700
Asn Ala Asp Lys Gly Phe Gly Phe Ile Thr Pro Asp Asp Gly Ser Lys
         15                  20                  25 gat gtg ttc gta cac ttc tct gct atg cag aac gat ggt tac aaa tct        748
Asp Val Phe Val His Phe Ser Ala Met Gln Asn Asp Gly Tyr Lys Ser
     30                  35                  40 ctg gac gaa ggt cag aaa gtg tcc ttc acc atg gaa agc ggc gct aaa        796
Leu Asp Glu Gly Gln Lys Val Ser Phe Thr Met Glu Ser Gly Ala Lys
 45                  50                  55                  60 ggc ccg gca gct ggt aac gta acc agc ctg taatctctgc ttaaaagcac         846
Gly Pro Ala Ala Gly Asn Val Thr Ser Leu
                 65                  70 agaatctaag atccctgcca tttggcgggg attttttat ttgttttcag gaaataaata      906
atcgatcgcg taataaaatc tattattatt tttgtgaaga ataaatttgg gtgcaatgag    966
aatgcgcaac gccgtaagta aggcgggaat aatttcccgc cgaagactct tactgtttca   1026
atttgcaggc taaaaacgcc gccagctcat aactctcctg tttaatatgc aattcacaca    1086
gtgaatctct tatcatgcag gtgaaaaata aaagcgtgaa acaaatcact attaaagaaa    1146
gtaatgtata tttctgcgca ttccagctct gtgttgattt cacgagtatg tagtgcacc     1205

<210> SEQ ID NO 2
<211> LENGTH: 70
<212> TYPE: PRT
<213> ORGANISM: E. coli

<400> SEQUENCE: 2

Met Ser Gly Lys Met Thr Gly Ile Val Lys Trp Phe Asn Ala Asp Lys
  1               5                  10                  15

Gly Phe Gly Phe Ile Thr Pro Asp Asp Gly Ser Lys Asp Val Phe Val
                 20                  25                  30

His Phe Ser Ala Met Gln Asn Asp Gly Tyr Lys Ser Leu Asp Glu Gly
             35                  40                  45

Gln Lys Val Ser Phe Thr Met Glu Ser Gly Ala Lys Gly Pro Ala Ala
         50                  55                  60

Gly Asn Val Thr Ser Leu
 65                  70

<210> SEQ ID NO 3
```

-continued

```
<211> LENGTH: 877
<212> TYPE: DNA
<213> ORGANISM: E. coli
<220> FEATURE:
<221> NAME/KEY: CDS
<222> LOCATION: (528)..(740)

<400> SEQUENCE: 3
agctttaata tagctcatga aagtaaaca ttggcagctg aagggccacg cagaccattt     60
atccggcaaa attccacgcg taatccggtg gtaatttctt ctgcatcgcg gagattgagc    120
gctgaaacat gaagctggac atcgatacga ccatcggatg gggtgataag acccttgccg    180
cttttgccgt caaggttttt gacaattcct gtcattttac gggacaaaaa aattccttaa    240
tactgataac ttggcgcact atacacacgt tcctgaagaa agctatagtt ttttgatggg    300
gttgaagatg gctggatgtc taaataaaac attgcttcat atgttcaact atgcgttaat    360
gattgcgtcg gtttgaagaa cagacgatat acgaagtagt ttactaaagc agttctcatt    420
tcaggtgtta ttcacttatt ccttctttga gtctctccaa ttaagtacga agtcgtttct    480
gttatgcaaa ccatttatgc cgaaaggctc aagttaagga atgtaga atg tca aat     536
                                                      Met Ser Asn
                                                       1 aaa atg act ggt tta gta aaa tgg ttt aac gct gat aaa ggt ttc ggc     584
Lys Met Thr Gly Leu Val Lys Trp Phe Asn Ala Asp Lys Gly Phe Gly
     5                  10                  15 ttt att tct cct gtt gat ggt agt aaa gat gtg ttt gtg cat ttt tct     632
Phe Ile Ser Pro Val Asp Gly Ser Lys Asp Val Phe Val His Phe Ser
 20                  25                  30                  35 gcg att cag aat gat aat tat cga acc tta ttt gaa ggt caa aag gtt     680
Ala Ile Gln Asn Asp Asn Tyr Arg Thr Leu Phe Glu Gly Gln Lys Val
             40                  45                  50 acc ttc tct ata gag agt ggt gct aaa ggt cct gca gca gca aat gtc     728
Thr Phe Ser Ile Glu Ser Gly Ala Lys Gly Pro Ala Ala Ala Asn Val
         55                  60                  65 atc att act gat taaaattcat cgctcgtctg tatacgataa cgaagaaggc         780
Ile Ile Thr Asp
         70 tgatgcctga gtagagatac ggacagagta gtgaatattg gatctcttta ataaaaagta    840 aggaggtcca atacatgaaa caatggctag catattt                             877

<210> SEQ ID NO 4
<211> LENGTH: 71
<212> TYPE: PRT
<213> ORGANISM: E. coli

<400> SEQUENCE: 4

Met Ser Asn Lys Met Thr Gly Leu Val Lys Trp Phe Asn Ala Asp Lys
 1               5                  10                  15

Gly Phe Gly Phe Ile Ser Pro Val Asp Gly Ser Lys Asp Val Phe Val
                20                  25                  30

His Phe Ser Ala Ile Gln Asn Asp Asn Tyr Arg Thr Leu Phe Glu Gly
         35                  40                  45

Gln Lys Val Thr Phe Ser Ile Glu Ser Gly Ala Lys Gly Pro Ala Ala
     50                  55                  60

Ala Asn Val Ile Ile Thr Asp
 65                  70

<210> SEQ ID NO 5
<211> LENGTH: 2863
```

-continued

```
<212> TYPE: DNA
<213> ORGANISM: E. coli
<220> FEATURE:
<221> NAME/KEY: CDS
<222> LOCATION: (938)..(2704)

<400> SEQUENCE: 5
```

| | |
|---|---:|
| gtgattctgg cacgtatgga acaaatcctt gccagtcggg ctttaaccga tgacgaacgc | 60 |
| gcacagcttt tatatgagcg cggagtgttg tatgatagtc tcggtctgag ggcattagcg | 120 |
| cgtaacgatt tttcgcaagc gctggcaatc cgaccggata tgcctgaagt attcaattac | 180 |
| ttagccatat attaacgcag gcaggcaatt ttgatcgtgc ctatgaagcg tttgttctgt | 240 |
| acttgagctt gatccaactt acaactacgc gcacttgatc gcgggatcgc attatattac | 300 |
| ggcggtcgtg acaagttagc gcaagatgat ctgctggcgt ttaacttgac gatcccaatg | 360 |
| atcctttccg tagtctgtgg ctttatctcg ccgagcagaa gctcgatgag aagcaggcta | 420 |
| aagaagtgtt gaaacagcac ttcgaaaaat cggataagga acagtgggga tggaacattg | 480 |
| tcgagttcta cctgggcaac attagcgaac aaacgttaat ggaaaggctc aaggcggacg | 540 |
| caacggataa cacctcgctc gctgagcatc tcagtgaaac caaccttcta tttaggtaag | 600 |
| tactacctaa gtctggggga tttggacagc gccacggcac tgttcaactg gaggttgcca | 660 |
| acaacgttca taactttgtt gagcaccgat acgcattgtt ggaattatcg ctcctgggcc | 720 |
| aggaccaaga tgacctggca gaatcggacc agcaatagct gacgtacaca tcagcccgta | 780 |
| atcttttttg attgccatca ccttaacggg tgagggcgtt gttgttcgtt aatacaccta | 840 |
| ctttgagccg gttcacactt ttcaatgaaa attgctgatc aatttcatga tgagttatgt | 900 |
| agactggccg ccattaattt tgaggcacac gtactac atg gct gaa ttc gaa acc | 955 |
|                                                                     Met Ala Glu Phe Glu Thr | |
|                                                                       1              5 | |
| act ttt gca gat ctg ggc ctg aag gct cct atc ctt gaa gcc ctt aac | 1003 |
| Thr Phe Ala Asp Leu Gly Leu Lys Ala Pro Ile Leu Glu Ala Leu Asn | |
|            10                  15                  20 | |
| gat ctg ggt tac gaa aaa cca tct cca att cag gca gag tgt att cca | 1051 |
| Asp Leu Gly Tyr Glu Lys Pro Ser Pro Ile Gln Ala Glu Cys Ile Pro | |
|      25                  30                  35 | |
| cat ctg ctg aat ggc cgc gac gtt ctg ggt atg gcc cag acg ggg agc | 1099 |
| His Leu Leu Asn Gly Arg Asp Val Leu Gly Met Ala Gln Thr Gly Ser | |
| 40                  45                  50 | |
| gga aaa act gca gca ttc tct tta cct ctg ttg cag aat ctt gat cct | 1147 |
| Gly Lys Thr Ala Ala Phe Ser Leu Pro Leu Leu Gln Asn Leu Asp Pro | |
| 55                  60                  65                  70 | |
| gag ctg aaa gca cca cag att ctg gtg ctg gca ccg acc cgc gaa ctg | 1195 |
| Glu Leu Lys Ala Pro Gln Ile Leu Val Leu Ala Pro Thr Arg Glu Leu | |
|                 75                  80                  85 | |
| gcg gta cag gtt gct gaa gca atg acg gat ttc tct aaa cac atg cgc | 1243 |
| Ala Val Gln Val Ala Glu Ala Met Thr Asp Phe Ser Lys His Met Arg | |
|           90                  95                 100 | |
| ggc gta aat gtg gtt gct ctg tac ggc ggc cag cgt tat gac gtg caa | 1291 |
| Gly Val Asn Val Val Ala Leu Tyr Gly Gly Gln Arg Tyr Asp Val Gln | |
|          105                 110                 115 | |
| tta cgc gcc ctg cgt cag ggg ccg cag atc gtt gtc ggt act ccg ggc | 1339 |
| Leu Arg Ala Leu Arg Gln Gly Pro Gln Ile Val Val Gly Thr Pro Gly | |
| 120                 125                 130 | |
| cgt ctg ctg gac cac ctg aaa cgt ggc act ctg gac ctc tct aaa ctg | 1387 |
| Arg Leu Leu Asp His Leu Lys Arg Gly Thr Leu Asp Leu Ser Lys Leu | |
| 135                 140                 145                 150 | |
| agc ggt ctg gtt ctg gat gaa gct gac gaa atg ctg cgc atg ggc ttc | 1435 |

```
Ser Gly Leu Val Leu Asp Glu Ala Asp Glu Met Leu Arg Met Gly Phe
            155                 160                 165 atc gaa gac gtt gaa acc att atg gcg cag atc ccg gaa ggt cat cag      1483
Ile Glu Asp Val Glu Thr Ile Met Ala Gln Ile Pro Glu Gly His Gln
            170                 175                 180 acc gct ctg ttc tct gca acc atg ccg gaa gcg att cgt cgc att acc      1531
Thr Ala Leu Phe Ser Ala Thr Met Pro Glu Ala Ile Arg Arg Ile Thr
            185                 190                 195 cgc cgc ttt atg aaa gag ccg cag gaa gtg cgc att cag tcc agc gtg      1579
Arg Arg Phe Met Lys Glu Pro Gln Glu Val Arg Ile Gln Ser Ser Val
        200                 205                 210 act acc cgt cct gac atc agc cag agc tac tgg act gtc tgg ggt atg      1627
Thr Thr Arg Pro Asp Ile Ser Gln Ser Tyr Trp Thr Val Trp Gly Met
215                 220                 225                 230 cgc aaa aac gaa gca ctg gta cgt ttc ctg gaa gcg gaa gat ttt gat      1675
Arg Lys Asn Glu Ala Leu Val Arg Phe Leu Glu Ala Glu Asp Phe Asp
                235                 240                 245 gcg gcg att atc ttc gtt cgt acc aaa aac gcg act ctg gaa gtg gct      1723
Ala Ala Ile Ile Phe Val Arg Thr Lys Asn Ala Thr Leu Glu Val Ala
            250                 255                 260 gaa gct ctt gag cgt aac ggc tac aac agc gcc gcg ctg aac ggt gac      1771
Glu Ala Leu Glu Arg Asn Gly Tyr Asn Ser Ala Ala Leu Asn Gly Asp
            265                 270                 275 atg aac cag gcg ctg cgt gaa cag aca ctg gaa cgc ctg aaa gat ggt      1819
Met Asn Gln Ala Leu Arg Glu Gln Thr Leu Glu Arg Leu Lys Asp Gly
        280                 285                 290 cgt ctg gac atc ctg att gcg acc gac gtt gca gcc cgt ggc ctg gac      1867
Arg Leu Asp Ile Leu Ile Ala Thr Asp Val Ala Ala Arg Gly Leu Asp
295                 300                 305                 310 gtt gag cgt atc agc ctg gta gtt aac tac gat atc ccg atg gat tct      1915
Val Glu Arg Ile Ser Leu Val Val Asn Tyr Asp Ile Pro Met Asp Ser
                315                 320                 325 gag tct tac gtt cac cgt atc ggt cgt acc ggt cgt gcg ggt cgt gct      1963
Glu Ser Tyr Val His Arg Ile Gly Arg Thr Gly Arg Ala Gly Arg Ala
            330                 335                 340 ggc cgc gcg ctg ctg ttc gtt gag aac cgc gag cgt cgt ctg ctg cgc      2011
Gly Arg Ala Leu Leu Phe Val Glu Asn Arg Glu Arg Arg Leu Leu Arg
        345                 350                 355 aac att gaa cgt act atg aag ctg act att ccg gaa gta gaa ctg ccg      2059
Asn Ile Glu Arg Thr Met Lys Leu Thr Ile Pro Glu Val Glu Leu Pro
360                 365                 370 aac gca gaa ctg cta ggc aaa cgc cgt ctg gaa aaa ttc gcc gct aaa      2107
Asn Ala Glu Leu Leu Gly Lys Arg Arg Leu Glu Lys Phe Ala Ala Lys
375                 380                 385                 390 gta cag cag cag ctg gaa agc agc gat ctg gat caa tac cgc gca ctg      2155
Val Gln Gln Gln Leu Glu Ser Ser Asp Leu Asp Gln Tyr Arg Ala Leu
                395                 400                 405 ctg agc aaa att cag ccg act gct gaa ggt gaa gag ctg gat ctc gaa      2203
Leu Ser Lys Ile Gln Pro Thr Ala Glu Gly Glu Glu Leu Asp Leu Glu
            410                 415                 420 act ctg gct gcg gca ctg ctg aaa atg gca cag ggt gaa cgt act ctg      2251
Thr Leu Ala Ala Ala Leu Leu Lys Met Ala Gln Gly Glu Arg Thr Leu
            425                 430                 435
atc gta ccg cca gat gcg ccg atg cgt ccg aaa cgt gaa ttc gtt gac      2299
Ile Val Pro Pro Asp Ala Pro Met Arg Pro Lys Arg Glu Phe Arg Asp
            440                 445                 450 cgt gat gac cgt ggt ccg cgc gat cgt aac gac cgt ggc ccg cgt ggt      2347
Arg Asp Asp Arg Gly Pro Arg Asp Arg Asn Asp Arg Gly Pro Arg Gly
455                 460                 465                 470 gac cgt gaa gat cgt ccg cgt cgt gaa cgt cgt gat gtt ggc gat atg      2395
```

-continued

```
                Asp Arg Glu Asp Arg Pro Arg Arg Glu Arg Arg Asp Val Gly Asp Met
                                475                 480                 485 cag ctg tac cgc att gaa gtg ggc cgc gat gat ggt gtt gaa gtt cgt         2443
Gln Leu Tyr Arg Ile Glu Val Gly Arg Asp Asp Gly Val Glu Val Arg
            490                 495                 500 cat atc gtt ggt gcg att gct aac gaa ggc gac atc agc agc cct tac         2491
His Ile Val Gly Ala Ile Ala Asn Glu Gly Asp Ile Ser Ser Pro Tyr
        505                 510                 515 att ggt aac atc aag ctg ttt gct tct cac tcc acc atc gaa ctg ccg         2539
Ile Gly Asn Ile Lys Leu Phe Ala Ser His Ser Thr Ile Glu Leu Pro
    520                 525                 530 aaa ggt atg ccg ggt gaa gtg ctg caa cac ttt acg cgc act cgc att         2587
Lys Gly Met Pro Gly Glu Val Leu Gln His Phe Thr Arg Thr Arg Ile
535                 540                 545                 550 ctc aac aag ccg atg aac atg cag tta ctg ggt cgt cgt ttt agc ggc         2635
Leu Asn Lys Pro Met Asn Met Gln Leu Leu Gly Arg Arg Phe Ser Gly
                555                 560                 565 gaa cgt cgt gaa ggc cgc gct ccg cgt cgt gat gat tct acc ggt cgt         2683
Glu Arg Arg Glu Gly Arg Ala Pro Arg Arg Asp Asp Ser Thr Gly Arg
            570                 575                 580 cgt cgt ttc ggt ggt gat gcg taatcatcgc tgaacagcga acacaatctg            2734
Arg Arg Phe Gly Gly Asp Ala
        585 taaaataata tatacagccc cgatttttac catcgggct tttttctgt cttttgtact         2794 cgtgtactgg tacagtgcaa tgcataacaa cgcagtcgca ctattttca ctggagagaa        2854 gccctcatg                                                               2863

<210> SEQ ID NO 6
<211> LENGTH: 589
<212> TYPE: PRT
<213> ORGANISM: E. coli

<400> SEQUENCE: 6

Met Ala Glu Phe Glu Thr Thr Phe Ala Asp Leu Gly Leu Lys Ala Pro
 1               5                  10                  15

Ile Leu Glu Ala Leu Asn Asp Leu Gly Tyr Glu Lys Pro Ser Pro Ile
            20                  25                  30

Gln Ala Glu Cys Ile Pro His Leu Leu Asn Gly Arg Asp Val Leu Gly
        35                  40                  45

Met Ala Gln Thr Gly Ser Gly Lys Thr Ala Ala Phe Ser Leu Pro Leu
    50                  55                  60

Leu Gln Asn Leu Asp Pro Glu Leu Lys Ala Pro Gln Ile Leu Val Leu
65                  70                  75                  80

Ala Pro Thr Arg Glu Leu Ala Val Gln Val Ala Glu Ala Met Thr Asp
                85                  90                  95

Phe Ser Lys His Met Arg Gly Val Asn Val Val Ala Leu Tyr Gly Gly
            100                 105                 110

Gln Arg Tyr Asp Val Gln Leu Arg Ala Leu Arg Gln Gly Pro Gln Ile
        115                 120                 125

Val Val Gly Thr Pro Gly Arg Leu Leu Asp His Leu Lys Arg Gly Thr
    130                 135                 140

Leu Asp Leu Ser Lys Leu Ser Gly Leu Val Leu Asp Glu Ala Asp Glu
145                 150                 155                 160

Met Leu Arg Met Gly Phe Ile Glu Asp Val Glu Thr Ile Met Ala Gln
                165                 170                 175

Ile Pro Glu Gly His Gln Thr Ala Leu Phe Ser Ala Thr Met Pro Glu
```

```
                    180                 185                 190
Ala Ile Arg Arg Ile Thr Arg Arg Phe Met Lys Glu Pro Gln Glu Val
                195                 200                 205
Arg Ile Gln Ser Ser Val Thr Thr Arg Pro Asp Ile Ser Gln Ser Tyr
            210                 215                 220
Trp Thr Val Trp Gly Met Arg Lys Asn Glu Ala Leu Val Arg Phe Leu
225                 230                 235                 240
Glu Ala Glu Asp Phe Asp Ala Ala Ile Ile Phe Val Arg Thr Lys Asn
                245                 250                 255
Ala Thr Leu Glu Val Ala Glu Ala Leu Glu Arg Asn Gly Tyr Asn Ser
                260                 265                 270
Ala Ala Leu Asn Gly Asp Met Asn Gln Ala Leu Arg Glu Gln Thr Leu
            275                 280                 285
Glu Arg Leu Lys Asp Gly Arg Leu Asp Ile Leu Ile Ala Thr Asp Val
            290                 295                 300
Ala Ala Arg Gly Leu Asp Val Glu Arg Ile Ser Leu Val Val Asn Tyr
305                 310                 315                 320
Asp Ile Pro Met Asp Ser Glu Ser Tyr Val His Arg Ile Gly Arg Thr
                325                 330                 335
Gly Arg Ala Gly Arg Ala Gly Arg Ala Leu Leu Phe Val Glu Asn Arg
            340                 345                 350
Glu Arg Arg Leu Leu Arg Asn Ile Glu Arg Thr Met Lys Leu Thr Ile
            355                 360                 365
Pro Glu Val Glu Leu Pro Asn Ala Glu Leu Leu Gly Lys Arg Arg Leu
370                 375                 380
Glu Lys Phe Ala Ala Lys Val Gln Gln Gln Leu Glu Ser Ser Asp Leu
385                 390                 395                 400
Asp Gln Tyr Arg Ala Leu Leu Ser Lys Ile Gln Pro Thr Ala Glu Gly
                405                 410                 415
Glu Glu Leu Asp Leu Glu Thr Leu Ala Ala Ala Leu Leu Lys Met Ala
            420                 425                 430
Gln Gly Glu Arg Thr Leu Ile Val Pro Pro Asp Ala Pro Met Arg Pro
            435                 440                 445
Lys Arg Glu Phe Arg Asp Arg Asp Arg Gly Pro Arg Asp Arg Asn
450                 455                 460
Asp Arg Gly Pro Arg Gly Asp Arg Glu Asp Arg Pro Arg Glu Arg
465                 470                 475                 480
Arg Asp Val Gly Asp Met Gln Leu Tyr Arg Ile Glu Val Gly Arg Asp
                485                 490                 495
Asp Gly Val Glu Val Arg His Ile Val Gly Ala Ile Ala Asn Glu Gly
            500                 505                 510
Asp Ile Ser Ser Pro Tyr Ile Gly Asn Ile Lys Leu Phe Ala Ser His
            515                 520                 525
Ser Thr Ile Glu Leu Pro Lys Gly Met Pro Gly Glu Val Leu Gln His
530                 535                 540
Phe Thr Arg Thr Arg Ile Leu Asn Lys Pro Met Asn Met Gln Leu Leu
545                 550                 555                 560
Gly Arg Arg Phe Ser Gly Glu Arg Arg Glu Gly Arg Ala Pro Arg Arg
                565                 570                 575
Asp Asp Ser Thr Gly Arg Arg Phe Gly Gly Asp Ala
            580                 585
```

<210> SEQ ID NO 7

-continued

```
<211> LENGTH: 18
<212> TYPE: RNA
<213> ORGANISM: E. coli

<400> SEQUENCE: 7
aguacuuagu guuucacc                                                    18

<210> SEQ ID NO 8
<211> LENGTH: 30
<212> TYPE: RNA
<213> ORGANISM: E. coli
<220> FEATURE:
<221> NAME/KEY: CDS
<222> LOCATION: (1)..(30)

<400> SEQUENCE: 8 aug ucc ggu aaa aug acu ggu auc gua aaa                                30
Met Ser Gly Lys Met Thr Gly Ile Val Lys
 1               5                  10

<210> SEQ ID NO 9
<211> LENGTH: 10
<212> TYPE: PRT
<213> ORGANISM: E. coli

<400> SEQUENCE: 9

Met Ser Gly Lys Met Thr Gly Ile Val Lys
 1               5                  10

<210> SEQ ID NO 10
<211> LENGTH: 24
<212> TYPE: RNA
<213> ORGANISM: E. coli

<400> SEQUENCE: 10
ucgguuugaa gaacagacga uaua                                             24

<210> SEQ ID NO 11
<211> LENGTH: 24
<212> TYPE: RNA
<213> ORGANISM: E. coli

<400> SEQUENCE: 11
acgguuugac guacagacca uuaa                                             24

<210> SEQ ID NO 12
<211> LENGTH: 24
<212> TYPE: RNA
<213> ORGANISM: E. coli

<400> SEQUENCE: 12
aauagcugac guacacaauc agcc                                             24

<210> SEQ ID NO 13
<211> LENGTH: 11
<212> TYPE: RNA
<213> ORGANISM: E. coli
<220> FEATURE:
<223> OTHER INFORMATION: consensus

<400> SEQUENCE: 13
ugacguacag a                                                           11

<210> SEQ ID NO 14
<211> LENGTH: 19
```

```
<212> TYPE: RNA
<213> ORGANISM: E. coli

<400> SEQUENCE: 14
cgguuugacg uacagacca                                                   19

<210> SEQ ID NO 15
<211> LENGTH: 23
<212> TYPE: RNA
<213> ORGANISM: E. coli

<400> SEQUENCE: 15
gcgucgguuu gaagaacaga cga                                              23

<210> SEQ ID NO 16
<211> LENGTH: 24
<212> TYPE: RNA
<213> ORGANISM: E. coli

<400> SEQUENCE: 16
ggccaggacc aagaugaccu ggca                                             24

<210> SEQ ID NO 17
<211> LENGTH: 14
<212> TYPE: RNA
<213> ORGANISM: E. coli

<400> SEQUENCE: 17
acuuugugau ucau                                                        14

<210> SEQ ID NO 18
<211> LENGTH: 14
<212> TYPE: RNA
<213> ORGANISM: E. coli

<400> SEQUENCE: 18
augacuggua ucgu                                                        14

<210> SEQ ID NO 19
<211> LENGTH: 14
<212> TYPE: RNA
<213> ORGANISM: E. coli

<400> SEQUENCE: 19
augacugguu ucgu                                                        14

<210> SEQ ID NO 20
<211> LENGTH: 14
<212> TYPE: RNA
<213> ORGANISM: E. coli

<400> SEQUENCE: 20
augacugguu uagu                                                        14

<210> SEQ ID NO 21
<211> LENGTH: 14
<212> TYPE: RNA
<213> ORGANISM: E. coli

<400> SEQUENCE: 21
augaguuaug uaga                                                        14

<210> SEQ ID NO 22
```

```
<211> LENGTH: 14
<212> TYPE: RNA
<213> ORGANISM: E. coli

<400> SEQUENCE: 22
auggcgaaaa gaau                                                              14

<210> SEQ ID NO 23
<211> LENGTH: 47
<212> TYPE: RNA
<213> ORGANISM: Artificial Sequence
<220> FEATURE:
<223> OTHER INFORMATION: Description of Artificial Sequence: mRNA
      construct
<220> FEATURE:
<223> OTHER INFORMATION: n = g, c, u, or a
<220> FEATURE:
<223> OTHER INFORMATION: This sequence may encompass a construct wherein
      the "n" region may be 0-30.

<400> SEQUENCE: 23
augnnnnnnn nnnnnnnnnn nnnnnnnnnn nnnaugacug guaucgu                          47

<210> SEQ ID NO 24
<211> LENGTH: 47
<212> TYPE: DNA
<213> ORGANISM: Artificial Sequence
<220> FEATURE:
<223> OTHER INFORMATION: Description of Artificial Sequence: DNA which
      encodes for the mRNA construct
<220> FEATURE:
<223> OTHER INFORMATION: n = g, c, t, or a
<220> FEATURE:
<223> OTHER INFORMATION: This sequence may encompass a construct wherein
      the "n" region may be 0-30.

<400> SEQUENCE: 24
atgnnnnnnn nnnnnnnnnn nnnnnnnnnn nnnatgactg gtatcgt                          47

<210> SEQ ID NO 25
<211> LENGTH: 15
<212> TYPE: DNA
<213> ORGANISM: Artificial Sequence
<220> FEATURE:
<223> OTHER INFORMATION: Description of Artificial Sequence: DNA
      construct
<220> FEATURE:
<221> NAME/KEY: MOD_RES
<220> FEATURE: (5)
<223> OTHER INFORMATION: a substituted by t
<220> FEATURE:
<221> NAME/KEY: MOD_RES
<220> FEATURE: (6)
<223> OTHER INFORMATION: t substituted by c
<220> FEATURE:
<221> NAME/KEY: MOD_RES
<220> FEATURE: (9)
<223> OTHER INFORMATION: a substituted by g

<400> SEQUENCE: 25
aattnntana ggtaa                                                             15

<210> SEQ ID NO 26
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 26
```

-continued

```
gacaggatta aaaatcgatg                                            20

<210> SEQ ID NO 27
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 27
tttagagcca tcgtcaggag                                            20

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 28
acgataccag tcgattttac cggac                                      25

<210> SEQ ID NO 29
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 29
ctgtcgactt acttacggcg ttgc                                       24

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: Constructed
      peptide

<400> SEQUENCE: 30

Gly Gly Ile Pro Ser Leu Asp Pro
  1               5

<210> SEQ ID NO 31
<211> LENGTH: 7
<212> TYPE: PRT
<213> ORGANISM: Artificial Sequence
<220> FEATURE:
<223> OTHER INFORMATION: Description of Artificial Sequence: Constructed
      peptide

<400> SEQUENCE: 31

Met Lys Gly Gly Ile Pro Ser
  1               5

<210> SEQ ID NO 32
<211> LENGTH: 13
<212> TYPE: PRT
<213> ORGANISM: Artificial Sequence
<220> FEATURE:
<223> OTHER INFORMATION: Description of Artificial Sequence: Constructed
      peptide

<400> SEQUENCE: 32

Met Ser Gly Lys Met Thr Gly Ile Val Lys Trp Phe Asn
  1               5                  10
```

-continued

```
<210> SEQ ID NO 33
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 33
cgtctagagg gtattaataa tgtccggtaa aatgac                               36

<210> SEQ ID NO 34
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 34
cgccagggtt ttcccagtca cgac                                           24

<210> SEQ ID NO 35
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 35
cgtctagagg taatacacta tgaaaggggg aattcc                              36

<210> SEQ ID NO 36
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 36
ctagaggtaa tacactatgt ccggtaag                                       28

<210> SEQ ID NO 37
<211> LENGTH: 28
<212> TYPE: DNA
<213> ORGANISM: Artificial Sequence
<220> FEATURE:
<223> OTHER INFORMATION: Description of Artificial Sequence: Primer

<400> SEQUENCE: 37
gatccttacc ggacatagtg tattacct                                       28

<210> SEQ ID NO 38
<211> LENGTH: 15
<212> TYPE: DNA
<213> ORGANISM: E. coli
<220> FEATURE:
<223> OTHER INFORMATION: Transcription initiation site

<400> SEQUENCE: 38
acggttctag acgta                                                     15

<210> SEQ ID NO 39
<211> LENGTH: 20
<212> TYPE: DNA
<213> ORGANISM: Artificial Sequence
<220> FEATURE:
```

<223> OTHER INFORMATION: Description of Artificial Sequence: Primer

<400> SEQUENCE: 39
cggcattaag taagcagttg                                        20

<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 40
ctggatcctt taatggtctg tacgtcaaac cgt                          33

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Primer

<400> SEQUENCE: 41
cggaattcag cctgtaatct ct                                     22

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 42
ctgtcgactt acttacggcg ttgc                                   24

<210> SEQ ID NO 43
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 43
gacaggatta aaaatcgag                                         19

<210> SEQ ID NO 44
<211> LENGTH: 15
<212> TYPE: DNA
<213> ORGANISM: Artificial Sequence
<220> FEATURE:
<223> OTHER INFORMATION: Description of Artificial Sequence: Primer

<400> SEQUENCE: 44
aaccgttgat gtgca                                             15

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 45
taattaagtg tgcctttcgg                                        20

<210> SEQ ID NO 46
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 46
tttagagcca tcgtcaggag                                              20

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 47
ttcacacagg aaacagctat                                              20

<210> SEQ ID NO 48
<211> LENGTH: 159
<212> TYPE: DNA
<213> ORGANISM: E. coli
<220> FEATURE:
<223> OTHER INFORMATION: CspA 5'UTR

<400> SEQUENCE: 48
acggtttgac gtacagacca ttaaagcagt gtagtaaggc aagtcccttc aagagttatc     60
gttgataccc ctcgtagtgc acattccttt aacgcttcaa aatctgtaaa gcacgccata   120
tcgccgaaag gcacacttaa ttattaaagg taatacact                          159

<210> SEQ ID NO 49
<211> LENGTH: 600
<212> TYPE: DNA
<213> ORGANISM: E. coli
<220> FEATURE:
<223> OTHER INFORMATION: CspA (-457 to +143)

<400> SEQUENCE: 49
aagcttcgat gcaattcacg atcccgcagt gtgatttgag gagttttcaa tggaatataa     60
agatccaatg catgagctgt tgagcagcct ggaacagatt gtttttaaag atgaaacgca   120
gaaaattacc ctgacgcaca gaacaacgtc ctgtaccgaa attgagcagt tacgaaaagg   180
gacaggatta aaaatggatg atttcgcccg ggttttgggc gtatcagtcg ccatggtaaa   240
ggaatgggaa tccagacgcg tgaagccttc aagtgccgaa ctaaaattga tgcgtttgat   300
tcaagccaac ccgcattaa gtaagcagtt gatggaatag actttatcca cttatgctgt   360
ttacggtcct gatgacagac cgttttccaa ccgattaatc ataaatatga aaataattg   420 ttgcatcacc cgccaatgcg tggcttaatg cacatcaacg gtttgacgta cagaccatta   480
aagcagtgta gtaaggcaag tcccttcaag agttatcgtt gataccctc gtagtgcaca   540 ttcctttaac gcttcaaaat ctgtaaagca cgccatatcg ccgaaaggca cacttaatta   600

<210> SEQ ID NO 50
<211> LENGTH: 414
<212> TYPE: DNA
<213> ORGANISM: E. coli
<220> FEATURE:
<223> OTHER INFORMATION: CspA (-271 to +143)

<400> SEQUENCE: 50

-continued

| | |
|---|---|
| attaaaaatg gatgatttcg cccgggtttt gggcgtatca gtcgccatgg taaaggaatg | 60 |
| ggaatccaga cgcgtgaagc cttcaagtgc cgaactaaaa ttgatgcgtt tgattcaagc | 120 |
| caacccggca ttaagtaagc agttgatgga atagacttta tccacttatg ctgtttacgg | 180 |
| tcctgatgac agaccgtttt ccaaccgatt aatcataaat atgaaaaata attgttgcat | 240 |
| cacccgccaa tgcgtggctt aatgcacatc aacggtttga cgtacagacc attaaagcag | 300 |
| tgtagtaagg caagtccctt caagagttat cgttgatacc cctcgtagtg cacattcctt | 360 |
| taacgcttca aatctgtaa agcacgccat atcgccgaaa ggcacactta atta | 414 |

<210> SEQ ID NO 51
<211> LENGTH: 288
<212> TYPE: DNA
<213> ORGANISM: E. coli
<220> FEATURE:
<223> OTHER INFORMATION: CspA (-145 to +143)

<400> SEQUENCE: 51

| | |
|---|---|
| ggcattaagt aagcagttga tggaatagac tttatccact tatgctgttt acggtcctga | 60 |
| tgacagaccg ttttccaacc gattaatcat aaatatgaaa ataattgtt gcatcacccg | 120 |
| ccaatgcgtg gcttaatgca catcaacggt ttgacgtaca gaccattaaa gcagtgtagt | 180 |
| aaggcaagtc ccttcaagag ttatcgttga taccctcgt agtgcacatt cctttaacgc | 240 |
| ttcaaaatct gtaaagcacg ccatatcgcc gaaaggcaca cttaatta | 288 |

<210> SEQ ID NO 52
<211> LENGTH: 234
<212> TYPE: DNA
<213> ORGANISM: E. coli
<220> FEATURE:
<223> OTHER INFORMATION: CspA (-91 to +143)

<400> SEQUENCE: 52

| | |
|---|---|
| tcctgatgac agaccgtttt ccaaccgatt aatcataaat atgaaaaata attgttgcat | 60 |
| cacccgccaa tgcgtggctt aatgcacatc aacggtttga cgtacagacc attaaagcag | 120 |
| tgtagtaagg caagtccctt caagagttat cgttgatacc cctcgtagtg cacattcctt | 180 |
| taacgcttca aatctgtaa agcacgccat atcgccgaaa ggcacactta atta | 234 |

<210> SEQ ID NO 53
<211> LENGTH: 210
<212> TYPE: DNA
<213> ORGANISM: E. coli
<220> FEATURE:
<223> OTHER INFORMATION: CspA (-67 to +143)

<400> SEQUENCE: 53

| | |
|---|---|
| ccgattaatc ataaatatga aaataattg ttgcatcacc cgccaatgcg tggcttaatg | 60 |
| cacatcaacg gtttgacgta cagaccatta aagcagtgta gtaaggcaag tcccttcaag | 120 |
| agttatcgtt gataccctc gtagtgcaca ttcctttaac gcttcaaaat ctgtaaagca | 180 |
| cgccatatcg ccgaaaggca cttaatta | 210 |

<210> SEQ ID NO 54
<211> LENGTH: 161
<212> TYPE: DNA
<213> ORGANISM: E. coli
<220> FEATURE:

<400> SEQUENCE: 54

-continued

```
gtcggtttga agaacagacg atatacgaag tagtttacta aagcagttct catttcaggt      60
gttattcact tattccttct ttgagtctct ccaattaagt acgaagtcgt ttctgttatg     120
caaaccattt atgccgaaag gctcaagtta aggaatgtag a                         161
```

<210> SEQ ID NO 55
<211> LENGTH: 226
<212> TYPE: DNA
<213> ORGANISM: E. coli
<220> FEATURE:
<223> OTHER INFORMATION: CsdA 5' UTR

<400> SEQUENCE: 55

```
acaacgttca taactttgtt gagcaccgat acgcattgtt ggaattatcg ctcctgggcc      60
aggaccaaga tgacctggca gaatcggacc agcaatagct gacgtacaca tcagcccgta    120
atcttttttg attgccatca ccttaacggg tgagggcgtt gttgttcgtt aatacaccta    180
ctttgagccg gttcacactt ttcaatgaaa attgctgatc aatttc                   226
```

<210> SEQ ID NO 56
<211> LENGTH: 457
<212> TYPE: DNA
<213> ORGANISM: E. coli
<220> FEATURE:
<223> OTHER INFORMATION: CspA promoter

<400> SEQUENCE: 56

```
aagcttcgat gcaattcacg atcccgcagt gtgatttgag gagttttcaa tggaatataa      60
agatccaatg catgagctgt tgagcagcct ggaacagatt gtttttaaag atgaaacgca    120
gaaaattacc ctgacgcaca gaacaacgtc ctgtaccgaa attgagcagt tacgaaaagg    180
gacaggatta aaaatggatg atttcgcccg ggttttgggc gtatcagtcg ccatggtaaa    240
ggaatgggaa tccagacgcg tgaagccttc aagtgccgaa ctaaaattga tgcgtttgat    300
tcaagccaac ccggcattaa gtaagcagtt gatggaatag actttatcca cttatgctgt    360
ttacggtcct gatgacagac cgttttccaa ccgattaatc ataaatatga aaataattg     420 ttgcatcacc cgccaatgcg tggcttaatg cacatca                             457
```

<210> SEQ ID NO 57
<211> LENGTH: 366
<212> TYPE: DNA
<213> ORGANISM: E. coli
<220> FEATURE:
<223> OTHER INFORMATION: CspB promoter

<400> SEQUENCE: 57

```
agctttaata tagctcatga aggtaaaca ttggcagctg aagggccacg cagaccattt       60
atccggcaaa attccacgcg taatccggtg gtaatttctt ctgcatcgcg gagattgagc    120
gctgaaacat gaagctggac atcgatacga ccatcggatg gggtgataag acccttgccg    180
cttttgccgt caaggttttt gacaattcct gtcattttac gggacaaaaa aattccttaa    240
tactgataac ttggcgcact atacacacgt tcctgaagaa agctatagtt ttttgatggg    300
gttgaagatg gctggatgtc taaaataaac attgcttcat atgttcaact atgcgttaat    360
gattgc                                                               366
```

<210> SEQ ID NO 58
<211> LENGTH: 660
<212> TYPE: DNA
<213> ORGANISM: E. coli

-continued

<220> FEATURE:
<223> OTHER INFORMATION: CsdA promoter

<400> SEQUENCE: 58

```
gtgattctgg cacgtatgga acaaatcctt gccagtcggg ctttaaccga tgacgaacgc      60
gcacagcttt tatatgagcg cggagtgttg tatgatagtc tcggtctgag ggcattagcg     120
cgtaacgatt tttcgcaagc gctggcaatc cgaccggata tgcctgaagt attcaattac     180
ttagccatat attaacgcag gcaggcaatt ttgatgctgc ctatgaagcg tttgttctgt     240
acttgagctt gatccaactt acaactacgc gcacttgatc gcgggatcgc attatattac     300
ggcggtcgtg acaagttagc gcaagatgat ctgctggcgt ttaacttgac gatcccaatg     360
atcctttccg tagtctgtgg ctttatctcg ccgagcagaa gctcgatgag aagcaggcta     420
aagaagtgtt gaaacagcac ttcgaaaaat cggataagga acagtgggga tggaacattg     480
tcgagttcta cctgggcaac attagcgaac aaacgttaat ggaaaggctc aaggcggacg     540
caacggataa cacctcgctc gctgagcatc tcagtgaaac caaccttcta tttaggtaag     600
tactacctaa gtctggggga tttggacagc gccacggcac tgttcaactg gaggttgcca     660
```